United States Patent
Pathak

(10) Patent No.: US 9,333,279 B2
(45) Date of Patent: *May 10, 2016

(54) COATED STENT COMPRISING AN HMG-COA REDUCTASE INHIBITOR

(71) Applicant: Covidien LP, Mansfield, MA (US)

(72) Inventor: Chandrashekhar Pathak, Austin, TX (US)

(73) Assignee: Covidien Lp, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/539,148

(22) Filed: Nov. 12, 2014

(65) Prior Publication Data

US 2015/0140061 A1  May 21, 2015

Related U.S. Application Data

(63) Continuation of application No. 13/835,370, filed on Mar. 15, 2013, now Pat. No. 8,900,618, which is a continuation of application No. 12/891,953, filed on Sep. 28, 2010, now Pat. No. 8,449,905, which is a continuation of application No. 11/959,889, filed on Dec. 19, 2007, now Pat. No. 7,829,111, which is a continuation of application No. 10/027,374, filed on Dec. 21, 2001, now Pat. No. 7,323,189, which is a continuation-in-part of application No. 09/991,235, filed on Oct. 22, 2001, now abandoned.

(51) Int. Cl.
| | |
|---|---|
| *A61F 2/02* | (2006.01) |
| *A61L 31/12* | (2006.01) |
| *A61F 2/91* | (2013.01) |
| *A61L 31/08* | (2006.01) |
| *A61L 31/16* | (2006.01) |
| *A61F 2/82* | (2013.01) |
| *A61L 2/16* | (2006.01) |

(Continued)

(52) U.S. Cl.
CPC ............... *A61L 31/125* (2013.01); *A61F 2/82* (2013.01); *A61F 2/91* (2013.01); *A61L 2/16* (2013.01); *A61L 2/28* (2013.01); *A61L 31/048* (2013.01); *A61L 31/049* (2013.01); *A61L 31/06* (2013.01); *A61L 31/08* (2013.01); *A61L 31/10* (2013.01); *A61L 31/16* (2013.01); *A61F 2230/0013* (2013.01); *A61F 2250/0067* (2013.01); *A61L 2300/416* (2013.01); *A61L 2300/434* (2013.01); *A61L 2300/602* (2013.01); *A61L 2300/606* (2013.01); *A61L 2300/802* (2013.01); *A61L 2420/04* (2013.01)

(58) Field of Classification Search
CPC ........................................................ A61F 2/91
See application file for complete search history.

(56) References Cited

U.S. PATENT DOCUMENTS

| | | | |
|---|---|---|---|
| 4,451,568 | A | 5/1984 | Schneider et al. |
| 4,768,507 | A | 9/1988 | Fischell et al. |

(Continued)

FOREIGN PATENT DOCUMENTS

| | | |
|---|---|---|
| EP | 034 721 A2 | 9/1981 |
| EP | 0734721 A2 | 10/1996 |
| WO | 00/62830 A2 | 10/2000 |

OTHER PUBLICATIONS

Auer, J. et al., "Clinical Significance of Pleiotropic Effects of Statins: Lipid Reduction and Beyond," Current Medicinal Chemistry, vol. 9, No. 20, pp. 1831-1850 (2002).

*Primary Examiner* — Carlos Azpuru

(57) ABSTRACT

Stents with coatings comprising a combination of a restenosis inhibitor comprising an HMG-CoA reductase inhibitor and a carrier. Also provided are methods of coating stents with a combination of an HMG-CoA reductase inhibitor and a carrier. A preferred example of a restenosis inhibitor is cerivastatin. The stent coatings have been shown to release restenosis inhibitors in their active forms.

21 Claims, 7 Drawing Sheets

(51) Int. Cl.
    A61L 2/28    (2006.01)
    A61L 31/04   (2006.01)
    A61L 31/06   (2006.01)
    A61L 31/10   (2006.01)

(56) References Cited

U.S. PATENT DOCUMENTS

| | | |
|---|---|---|
| 4,795,458 A | 1/1989 | Regan |
| 4,952,419 A | 8/1990 | De Leon et al. |
| 5,015,253 A | 5/1991 | MacGregor |
| 5,059,211 A | 10/1991 | Stack et al. |
| 5,135,516 A | 8/1992 | Sahatjian et al. |
| 5,140,012 A | 8/1992 | McGovern et al. |
| 5,163,952 A | 11/1992 | Froix |
| 5,240,913 A | 8/1993 | Maraganore et al. |
| 5,258,020 A | 11/1993 | Froix |
| 5,282,824 A | 2/1994 | Gianturco |
| 5,292,321 A | 3/1994 | Lee |
| 5,292,331 A | 3/1994 | Boneau |
| 5,304,121 A | 4/1994 | Sahatjian |
| 5,314,688 A | 5/1994 | Kauffman et al. |
| 5,334,201 A | 8/1994 | Cowan |
| 5,366,504 A | 11/1994 | Andersen et al. |
| 5,380,299 A | 1/1995 | Fearnot et al. |
| 5,383,928 A | 1/1995 | Scott et al. |
| 5,405,378 A | 4/1995 | Strecker |
| 5,411,550 A | 5/1995 | Herweck et al. |
| 5,419,760 A | 5/1995 | Narciso, Jr. |
| 5,423,885 A | 6/1995 | Williams |
| 5,439,446 A | 8/1995 | Barry |
| 5,443,495 A | 8/1995 | Buscemi et al. |
| 5,449,382 A | 9/1995 | Dayton |
| 5,464,450 A | 11/1995 | Buscemi et al. |
| 5,464,650 A | 11/1995 | Berg et al. |
| 5,476,509 A | 12/1995 | Keogh et al. |
| 5,500,013 A | 3/1996 | Buscemi et al. |
| 5,507,771 A | 4/1996 | Gianturco |
| 5,545,208 A | 8/1996 | Wolff et al. |
| 5,545,211 A | 8/1996 | An et al. |
| 5,545,213 A | 8/1996 | Keogh et al. |
| 5,551,954 A | 9/1996 | Buscemi et al. |
| 5,554,182 A | 9/1996 | Dinh et al. |
| 5,556,413 A | 9/1996 | Lam |
| 5,571,086 A | 11/1996 | Kaplan et al. |
| 5,571,166 A | 11/1996 | Dinh et al. |
| 5,575,815 A | 11/1996 | Slepian et al. |
| 5,578,075 A | 11/1996 | Dayton |
| 5,588,352 A | 12/1996 | Harrison |
| 5,591,199 A | 1/1997 | Porter et al. |
| 5,591,227 A | 1/1997 | Dinh et al. |
| 5,593,434 A | 1/1997 | Williams |
| 5,599,352 A | 2/1997 | Dinh et al. |
| 5,603,722 A | 2/1997 | Phan et al. |
| 5,605,696 A | 2/1997 | Eury et al. |
| 5,607,467 A | 3/1997 | Froix |
| 5,609,629 A | 3/1997 | Fearnot et al. |
| 5,622,188 A | 4/1997 | Plaia et al. |
| 5,624,411 A | 4/1997 | Tuch |
| 5,628,785 A | 5/1997 | Schwartz et al. |
| 5,629,077 A | 5/1997 | Turnlund et al. |
| 5,632,771 A | 5/1997 | Boatman et al. |
| 5,632,840 A | 5/1997 | Campbell |
| 5,634,895 A | 6/1997 | Igo et al. |
| 5,637,113 A | 6/1997 | Tartaglia et al. |
| 5,649,977 A | 7/1997 | Campbell |
| 5,653,747 A | 8/1997 | Dereume |
| 5,670,161 A | 9/1997 | Healy et al. |
| 5,674,241 A | 10/1997 | Bley et al. |
| 5,674,242 A | 10/1997 | Phan et al. |
| 5,674,276 A | 10/1997 | Andersen et al. |
| 5,674,278 A | 10/1997 | Boneau |
| 5,674,287 A | 10/1997 | Slepian et al. |
| 5,697,967 A | 12/1997 | Dinh et al. |
| 5,700,286 A | 12/1997 | Tartaglia et al. |
| 5,713,949 A | 2/1998 | Jayaraman |
| 5,716,981 A | 2/1998 | Hunter et al. |
| 5,718,159 A | 2/1998 | Thompson |
| 5,718,713 A | 2/1998 | Frantzen |
| 5,725,549 A | 3/1998 | Lam |
| 5,728,751 A | 3/1998 | Patnaik |
| 5,733,327 A | 3/1998 | Igaki et al. |
| 5,766,710 A | 6/1998 | Turnlund et al. |
| 5,769,883 A | 6/1998 | Buscemi et al. |
| 5,772,629 A | 6/1998 | Kaplan |
| 5,772,668 A | 6/1998 | Summers et al. |
| 5,788,979 A | 8/1998 | All et al. |
| 5,797,887 A | 8/1998 | Rosen et al. |
| 5,800,538 A | 9/1998 | Slepian et al. |
| 5,804,318 A | 9/1998 | Pinchuk et al. |
| 5,824,045 A | 10/1998 | All |
| 5,824,049 A | 10/1998 | Ragheb et al. |
| 5,827,322 A | 10/1998 | Williams |
| 5,836,316 A | 11/1998 | Plaia et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,861,027 A | 1/1999 | Trapp |
| 5,871,538 A | 2/1999 | Dereume |
| 5,873,904 A | 2/1999 | Ragheb et al. |
| 5,876,433 A | 3/1999 | Lunn |
| 5,876,449 A | 3/1999 | Starck et al. |
| 5,879,382 A | 3/1999 | Boneau |
| 5,891,108 A | 4/1999 | Leone et al. |
| 5,891,196 A | 4/1999 | Lee et al. |
| 5,893,868 A | 4/1999 | Hanson et al. |
| 5,895,407 A | 4/1999 | Jayaraman |
| 5,900,246 A | 5/1999 | Lambert |
| 5,904,146 A | 5/1999 | Plaia et al. |
| 5,928,279 A | 7/1999 | Shannon et al. |
| 5,954,744 A | 9/1999 | Phan et al. |
| 5,968,093 A | 10/1999 | Kranz |
| 5,972,027 A | 10/1999 | Johnson |
| 5,976,155 A | 11/1999 | Foreman et al. |
| 5,976,169 A | 11/1999 | Imran |
| 5,980,551 A | 11/1999 | Summers et al. |
| 6,004,943 A | 12/1999 | Shi et al. |
| 6,010,530 A | 1/2000 | Goicoechea |
| 6,015,402 A | 1/2000 | Sahota |
| 6,015,430 A | 1/2000 | Wall |
| 6,019,789 A | 2/2000 | Dinh et al. |
| 6,033,434 A | 3/2000 | Borghi |
| 6,033,436 A | 3/2000 | Steinke et al. |
| 6,036,725 A | 3/2000 | Avellanet |
| 6,039,757 A | 3/2000 | Edwards et al. |
| 6,041,305 A | 3/2000 | Sakurai |
| 6,071,305 A | 6/2000 | Brown et al. |
| 6,077,298 A | 6/2000 | Tu et al. |
| 6,080,422 A | 6/2000 | Williams |
| 6,083,257 A | 7/2000 | Taylor et al. |
| 6,086,455 A | 7/2000 | Frantzen |
| 6,086,611 A | 7/2000 | Duffy et al. |
| 6,087,552 A | 7/2000 | Gregory |
| 6,090,134 A | 7/2000 | Tu et al. |
| 6,090,135 A | 7/2000 | Plaia et al. |
| 6,096,070 A | 8/2000 | Ragheb et al. |
| 6,099,561 A | 8/2000 | Alt |
| 6,099,562 A | 8/2000 | Ding et al. |
| 6,099,563 A | 8/2000 | Zhong |
| 6,100,443 A | 8/2000 | Sims et al. |
| 6,102,943 A | 8/2000 | McGuinness |
| 6,113,628 A | 9/2000 | Borghi |
| 6,120,523 A | 9/2000 | Crocker et al. |
| 6,120,535 A | 9/2000 | McDonald et al. |
| 6,120,536 A | 9/2000 | Ding et al. |
| 6,129,757 A | 10/2000 | Weadock |
| 6,133,242 A | 10/2000 | Zalewski et al. |
| 6,146,358 A | 11/2000 | Rowe |
| 6,149,681 A | 11/2000 | Houser et al. |
| 6,159,488 A | 12/2000 | Nagler et al. |
| 6,161,399 A | 12/2000 | Jayaraman |
| 6,165,209 A | 12/2000 | Patterson et al. |
| 6,168,619 B1 | 1/2001 | Dinh et al. |
| 6,171,232 B1 | 1/2001 | Papandreou et al. |
| 6,171,609 B1 | 1/2001 | Kunz |

(56) References Cited

U.S. PATENT DOCUMENTS

| | | |
|---|---|---|
| 6,174,326 B1 | 1/2001 | Kitaoka et al. |
| 6,174,329 B1 | 1/2001 | Callol et al. |
| 6,177,523 B1 | 1/2001 | Reich et al. |
| 6,183,353 B1 | 2/2001 | Frantzen |
| 6,187,035 B1 | 2/2001 | Jang et al. |
| 6,193,746 B1 | 2/2001 | Strecker |
| 6,197,047 B1 | 3/2001 | Kranz |
| 6,197,051 B1 | 3/2001 | Zhong |
| 6,206,915 B1 | 3/2001 | Fagan et al. |
| 6,206,916 B1 | 3/2001 | Furst |
| 6,210,436 B1 | 4/2001 | Weadock |
| 6,214,040 B1 | 4/2001 | Jayaraman |
| 6,214,042 B1 | 4/2001 | Jacobsen et al. |
| 6,214,115 B1 | 4/2001 | Taylor et al. |
| 6,217,607 B1 | 4/2001 | Alt |
| 6,221,099 B1 | 4/2001 | Andersen et al. |
| 6,224,626 B1 | 5/2001 | Steinke |
| 6,231,600 B1 | 5/2001 | Zhong |
| 6,240,616 B1 | 6/2001 | Yan |
| 6,241,691 B1 | 6/2001 | Ferrera et al. |
| 6,245,104 B1 | 6/2001 | Alt |
| 6,245,760 B1 | 6/2001 | He et al. |
| 6,248,129 B1 | 6/2001 | Froix |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,627 B1 | 7/2001 | Freidberg |
| 6,254,632 B1 | 7/2001 | Wu et al. |
| 6,255,277 B1 | 7/2001 | Stamler et al. |
| 6,258,121 B1 | 7/2001 | Yang et al. |
| 6,263,880 B1 | 7/2001 | Parker et al. |
| 6,264,690 B1 | 7/2001 | Von Oepen |
| 6,273,908 B1 | 8/2001 | Ndondo-Lay |
| 6,273,913 B1 | 8/2001 | Wright et al. |
| 6,280,411 B1 | 8/2001 | Lennox |
| 6,290,719 B1 | 9/2001 | Garberoglio |
| 6,290,722 B1 | 9/2001 | Wang |
| 6,299,604 B1 | 10/2001 | Ragheb et al. |
| 6,306,165 B1 | 10/2001 | Patnaik et al. |
| 6,306,166 B1 | 10/2001 | Barry et al. |
| 6,315,794 B1 | 11/2001 | Richter |
| 6,325,821 B1 | 12/2001 | Gaschino et al. |
| 6,331,186 B1 | 12/2001 | Wang et al. |
| 6,331,527 B1 | 12/2001 | Parmacek et al. |
| 6,368,658 B1 | 4/2002 | Schwarz et al. |
| 6,387,124 B1 | 5/2002 | Buscemi et al. |
| 6,451,373 B1 | 9/2002 | Hossainy et al. |
| 6,468,304 B1 | 10/2002 | Dubois-Rande et al. |
| 6,506,437 B1 | 1/2003 | Harish et al. |
| 7,622,135 B2 * | 11/2009 | Pathak ............ A61F 2/91 424/426 |
| 7,829,111 B2 * | 11/2010 | Pathak ............ A61F 2/91 424/423 |
| 8,449,905 B2 * | 5/2013 | Pathak ............ A61F 2/91 424/425 |
| 2001/0001128 A1 | 5/2001 | Holman et al. |
| 2001/0003161 A1 | 6/2001 | Vardi et al. |
| 2001/0007082 A1 | 7/2001 | Dusbabek et al. |
| 2001/0007083 A1 | 7/2001 | Roorda |
| 2001/0009982 A1 | 7/2001 | Ferrera et al. |
| 2001/0010014 A1 | 7/2001 | Trozera |
| 2001/0016726 A1 | 8/2001 | Dubrul et al. |
| 2001/0016770 A1 | 8/2001 | Allen et al. |
| 2001/0027340 A1 | 10/2001 | Wright et al. |
| 2001/0029351 A1 | 10/2001 | Falotico et al. |
| 2001/0032010 A1 | 10/2001 | Sandock |
| 2001/0032014 A1 | 10/2001 | Yang et al. |
| 2001/0037144 A1 | 11/2001 | Kim et al. |
| 2001/0037145 A1 | 11/2001 | Guruwaiya et al. |
| 2001/0041929 A1 | 11/2001 | Oepen |
| 2001/0044649 A1 | 11/2001 | Vallana et al. |
| 2001/0044650 A1 | 11/2001 | Simso et al. |
| 2001/0044651 A1 | 11/2001 | Steinke et al. |
| 2001/0044652 A1 | 11/2001 | Moore |
| 2001/0044655 A1 | 11/2001 | Patnaik et al. |
| 2001/0047202 A1 | 11/2001 | Slaikeu et al. |
| 2001/0053928 A1 | 12/2001 | Edelman et al. |
| 2001/0056299 A1 | 12/2001 | Thompson |
| 2002/0002353 A1 | 1/2002 | Michal et al. |
| 2002/0002396 A1 | 1/2002 | Fulkerson |
| 2002/0002398 A1 | 1/2002 | Voinov |
| 2002/0004678 A1 | 1/2002 | Easterling |
| 2002/0004679 A1 | 1/2002 | Eury et al. |
| 2002/0004680 A1 | 1/2002 | Plaia et al. |
| 2002/0005206 A1 | 1/2002 | Falotico et al. |
| 2002/0007209 A1 | 1/2002 | Scheerder et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0044654 A1 | 4/2002 | Maeda et al. |
| 2002/0065546 A1 | 5/2002 | Machan et al. |
| 2002/0111590 A1 | 8/2002 | Davila et al. |
| 2002/0120326 A1 | 8/2002 | Michal |
| 2002/0133224 A1 | 9/2002 | Bajgar et al. |
| 2003/0009213 A1 | 1/2003 | Yang |
| 2003/0125800 A1 | 7/2003 | Shulze et al. |

\* cited by examiner

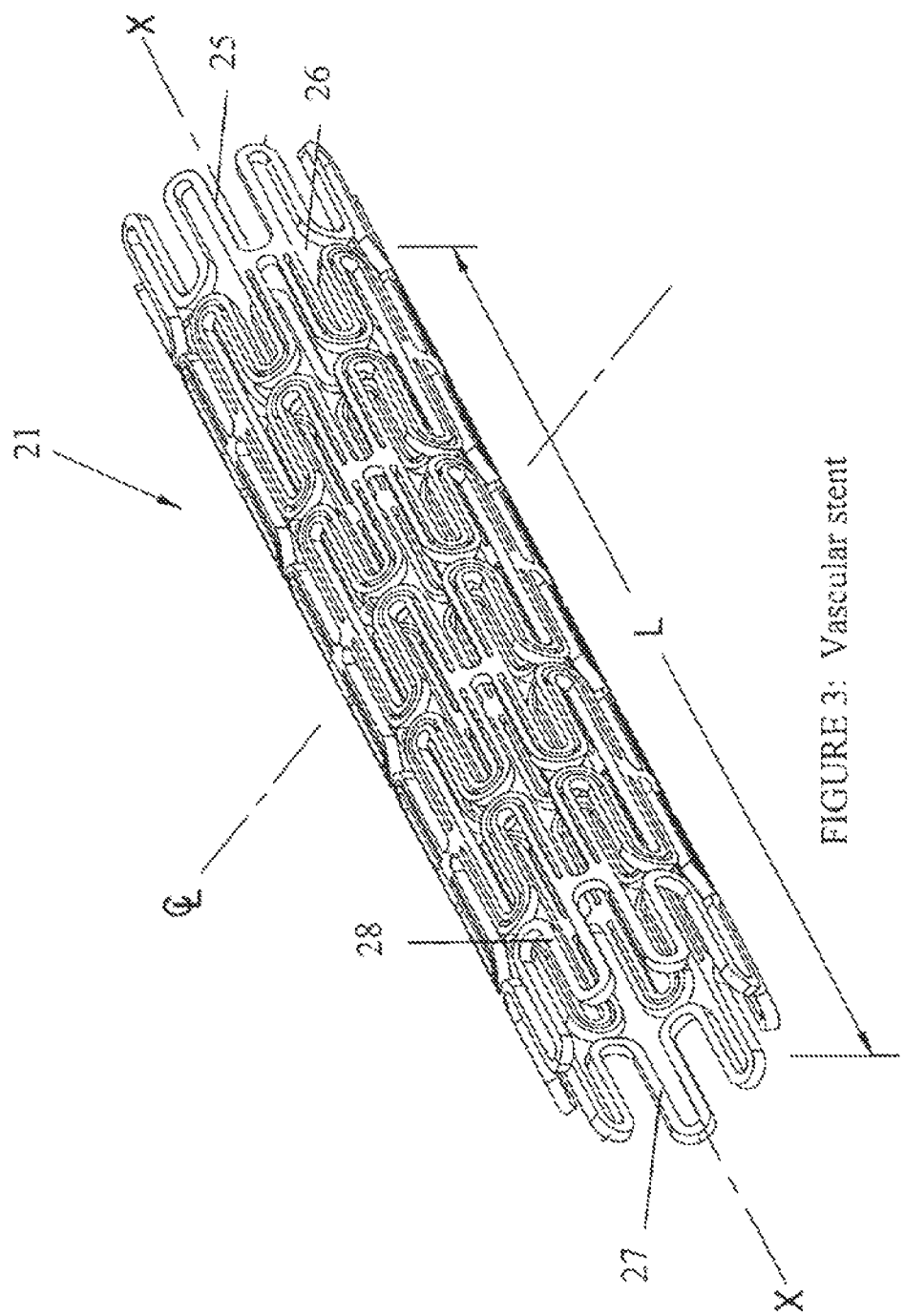
FIGURE 3: Vascular stent

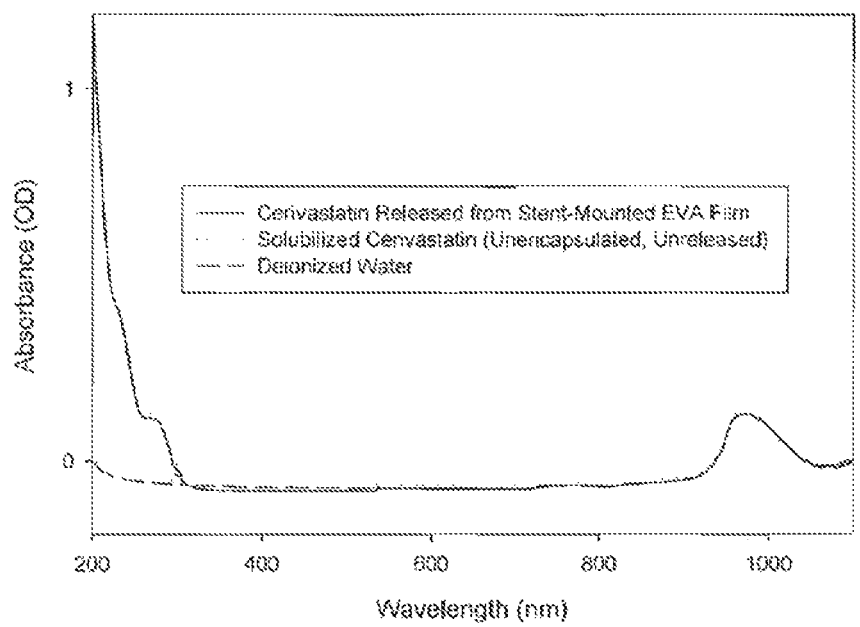
Figure 4: UV-VIS spectra comparison of cerivastatin released from EVA film and pure cerivastatin in deionized water

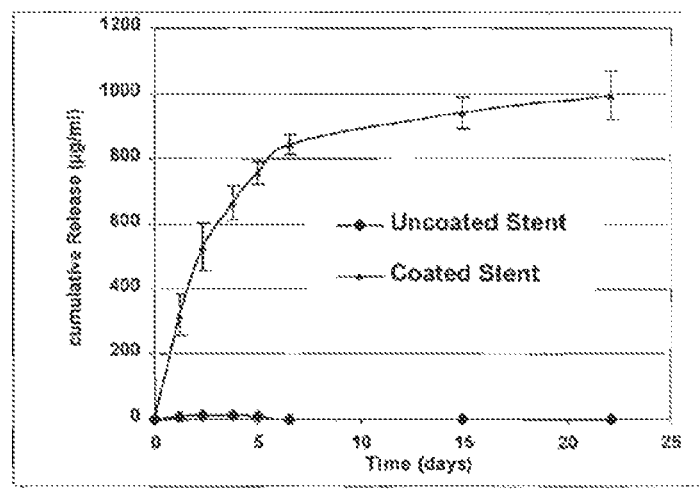
Figure 5: Cerivastatin release profile from EVA film wrapped on a stent

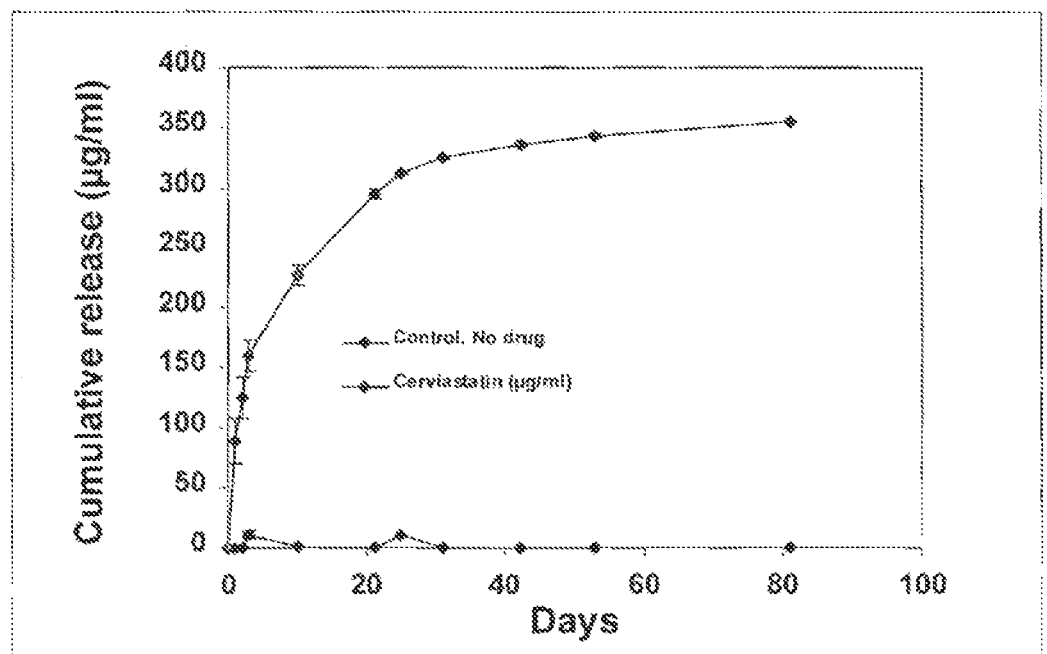
Figure 6: Cerivastatin release profile from polycaprolactone wrapped on the stent.

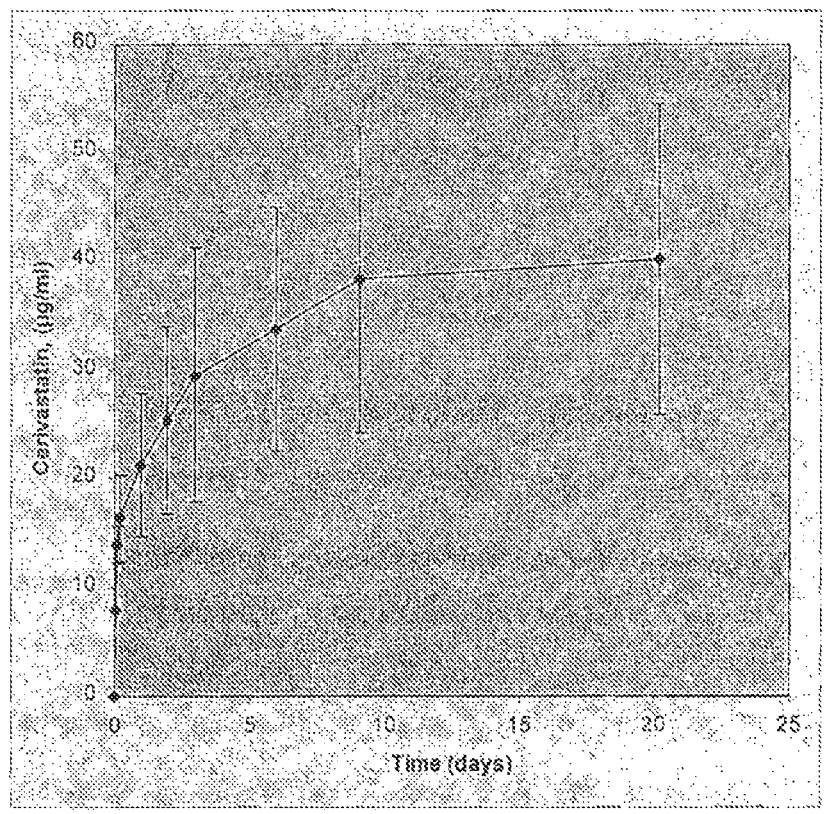
Figure 7: Release of cerivastatin from silicone coated stent

Figure 8: Release of cerivastatin from liquid vitamin E carrier
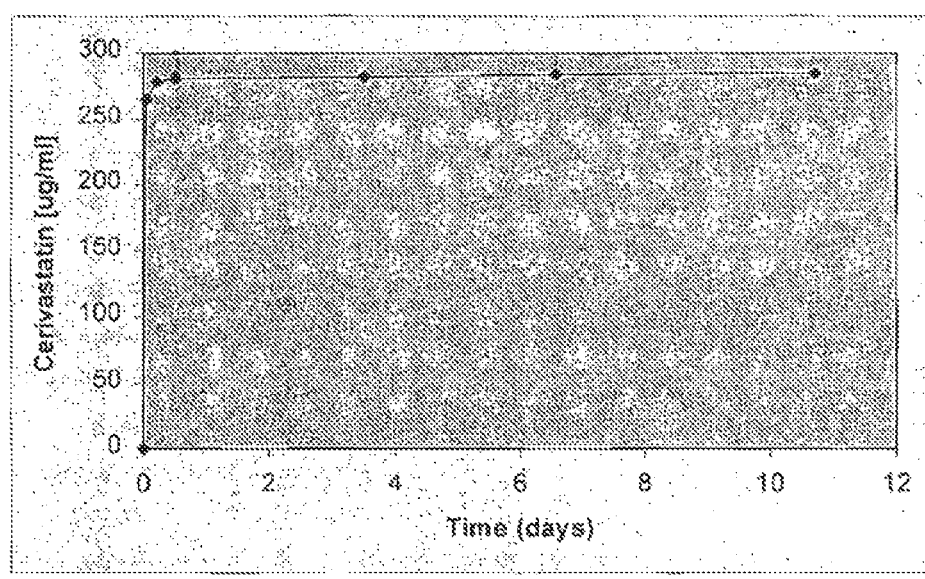

COATED STENT COMPRISING AN HMG-COA REDUCTASE INHIBITOR

RELATED APPLICATIONS

This application is a continuation of U.S. patent application Ser. No. 13/835,370, filed Mar. 15, 2013, which is a continuation of U.S. patent application Ser. No. 12/891,953, filed Sep. 28, 2010, now U.S. Pat. No. 8,449,905, which is a continuation of U.S. patent application Ser. No. 11/959,889, filed Dec. 19, 2007, now U.S. Pat. No. 7,829,111, which is a continuation of U.S. patent application Ser. No. 10/027,374 filed Dec. 21, 2001, now U.S. Pat. No. 7,323,189, which is a continuation-in-part of U.S. patent application Ser. No. 09/991,235, filed Oct. 22, 2001, now abandoned, the disclosures of which are incorporated herein by reference in their entirety.

BACKGROUND

1. Field of the Invention

The present invention generally relates to stent coatings that include bioactive compounds that inhibit restenosis.

2. Description of the Related Art

Stents are often used in the treatment of atherosclerosis, a disease of the vascular system in which arteries become partially, and sometimes completely, occluded with substances that may include lipids, cholesterol, calcium, and various types of cells, such as smooth muscle cells and platelets. Atherosclerosis is a very common disease that can be fatal, and methods of preventing the accumulation of occluding compounds in arteries are being investigated.

Percutaneous transluminal angioplasty (PTA) is a commonly used procedure to break up and/or remove already formed deposits along arterial walls. PTA can also be used to treat vascular occlusions not associated with atherosclerosis. During PTA, a catheter is threaded through a patient's arteries until the occluded area to be treated is reached. A balloon attached to the end of the catheter is then inflated at the occluded site. The expanded balloon breaks up the mass of occluding substances, resulting in a more open arterial lumen. However, there is a risk that the artery may re-close within a period of from one day to approximately six months of the procedure. This re-closure is known as restenosis. Accordingly, a balloon-only angioplasty procedure often does not result in a permanently reopened artery. To prevent restenosis, scaffolding devices called stents are deployed in the lumen of the artery as a structural support to maintain the lumen in an open state. Unlike the balloon and the catheter used in an angioplasty procedure, the stent usually remains in the artery as a permanent prosthesis. Although technically feasible, removal of the stent from the artery is generally avoided.

Stents are typically elongated structures used to keep open lumens (e.g., openings in the body) found in various parts of the body so that the parts of the body containing those lumens may function properly. Stents are usually implanted at their site of use in the body by attaching them in a compressed state to a catheter that is directed through the body to the site of stent use. The stent can be expanded to a size which enables it to keep the lumen open by supporting the walls of the lumen once it is positioned at the desired site.

The lumens of blood vessels are common sites of stent deployment. Vascular stents are frequently used in blood vessels to open the vessel and provide improved blood flow. The stents are typically hollow, cylindrical structures made from struts or interconnected filaments. Vascular stents can be collapsed to reduce their diameter so that the stent can be guided through a patients arteries or veins to reach the site of deployment. Stents are typically either coupled to the outside of the balloon for expansion by the expanding balloon or are self-expanding upon removal of a restraint such as a wire or sleeve maintaining the stent in its collapsed state.

The stent is allowed to expand at the desired site to a diameter large enough to keep the blood vessel open. Vascular stents are often made of metal to provide the strength necessary to support the occluded arterial walls. Two of the preferred metals are Nitinol alloys of nickel and titanium, and stainless steel. Other materials that can be used in fabricating stents are ceramics, polymers, and plastics. Stents may be coated with a substance, such as a biodegradable or biostable polymer, to improve the biocompatibility of the stent, making it less likely to cause an allergic or other immunological response in a patient. A coating substance may also add to the strength of the stent. Some known coating substances include organic acids, their derivatives, and synthetic polymers that are either biodegradable or biostable. Biostable coating substances do not degrade in the body, biodegradable coating substances can degrade in the body. A problem with known biodegradable and biostable stent coatings is that both types of coatings are susceptible to breaking and cracking during the temperature changes and expansion/contraction cycles experienced during stent formation and use.

Stents located within any lumen in the body may not always prevent partial or complete restenosis. In particular, stents do not always prevent the re-narrowing of an artery following PTA. In fact, the introduction and presence of the stent itself in the artery or vein can create regions of trauma such as, e.g., tears in the inner lining of the artery, called the endothelium. It is believed that such trauma can trigger migration of vascular smooth muscle cells, which are usually separated from the arterial lumen by the endothelium, into the arterial lumen, where they proliferate to create a mass of cells that may, in a matter of days or weeks, occlude the artery. Such re-occlusion, which is sometimes seen after PTA, is an example of restenosis. Coating a stent with a substance to make the surface of the stent smoother and to minimize damage to the endothelium has been one method used to create stents that are less likely to contribute to restenosis.

Currently, drug therapy for restenosis primarily consists of the systemic administration of drugs. However, delivering drugs in this manner may result in undesirable side effects in other areas of the body unrelated to the vascular occlusion. Also, the administered dose of a drug that is delivered systemically is less effective in achieving the desired effect in the local area of the body in which it is needed. For example, an anti-restenosis drug delivered systemically may be sequestered or metabolized by other parts of the body, resulting in only a small amount of the drug reaching the local area in which it is needed.

Stents with bioactive compounds or drugs in or on their coatings can be used. One class of drugs that can be used in stent coatings is restenosis inhibitors. There remains a need for coatings that can be shown to actually release the restenosis inhibiting compounds in their active forms. Further, there is a need for stents that can carry drugs and release them in a sufficient concentration to produce the desired effect. In particular, there is a need for such stents that can inhibit restenosis.

SUMMARY OF INVENTION

Broadly, the invention relates to coated stents, methods of making coated stents and methods of using coated stents. In one aspect, the invention can include a coated stent comprising a stent and a coating comprising a substantially unreacted HMG-CoA reductase inhibitor. It is preferred that the coating also comprise a carrier for the HMG-CoA reductase inhibitor. In a specific embodiment, the HMG-CoA reductase inhibitor is provided in a nonpolymeric carrier. In another embodiment, the HMG-CoA reductase inhibitor is provided in a polymeric carrier, which may be physically bound to the polymer, chemically bound to the polymer, or both. The coating composition can be a liquid solution at room and/or body temperature, which may include the HMG-CoA reductase inhibitor and the polymeric or nonpolymeric carrier, and which may additionally include a solvent which later may be removed, e.g., by drying. Alternatively, the coating composition may be a solid at room and body temperature.

The coating composition preferably includes an effective amount of the HMG-CoA reductase inhibitor. More particularly, the coating composition preferably includes an amount of the HMG-CoA reductase inhibitor that is sufficient to be therapeutically effective for inhibiting regrowth of plaque or inhibiting restenosis. In one embodiment, the coating composition may include from about 1 wt % to about 50 wt % HMG-CoA reductase inhibitor, based on the total weight of the coating composition. In another embodiment, the coating composition includes from about 5 wt % to about 30 wt % HMG-CoA reductase inhibitor. In yet another embodiment, the coating composition includes from about 10 wt % to about 20 wt % HMG-CoA reductase inhibitor. Any HMG-CoA reductase inhibitor may be used, but the HMG-CoA reductase inhibitor is preferably selected from the group consisting of cerivastatin, atorvastatin, simvastatin, fluvastatin, lovastatin, and pravastatin. More preferably, the HMG-CoA reductase inhibitor is cerivastatin. In another embodiment, the coating composition comprises more than one HMG-CoA reductase inhibitor. In another embodiment, the coating composition includes a restenosis inhibitor that is not an HMG-CoA reductase inhibitor.

In one embodiment, the coating composition comprises an effective amount of a polymeric carrier, e.g., an amount sufficient to provide a polymer matrix or support for the inhibitor. The polymer is preferably non-reactive with the HMG-CoA reductase inhibitor, i.e., no chemical reaction occurs when the two are mixed. The polymer may be a polymer having no functional groups. Alternatively, the polymer may be one having functional groups, but none that are reactive with the HMG-CoA reductase inhibitor. The polymer may include a biodegradable polymer. For example, the polymer may include a polymer selected from the group consisting of polyhydroxy acids, polyanhydrides, polyphosphazenes, polyalkylene oxalates, biodegradable polyamides, polyorthoesters, polyphosphoesters, polyorthocarbonates, and blends or copolymers thereof. The polymer may also include a biostable polymer, alone or in combination with a biodegradable polymer. For example, the polymer may include a polymer selected from the group consisting of polyurethanes, silicones, polyacrylates, polyesters, polyalkylene oxides, polyalcohols, polyolefins, polyvinyl chlorides, cellulose and its derivatives, fluorinated polymers, biostable polyamides, and blends or copolymers thereof.

At least certain embodiments of the invention provide a coated stent comprising a stent having a coating composition that includes a biologically active component and a biodegradable, low-melting carrier component. Accordingly, in one embodiment, the invention provides a stent having a coating composition comprising a biologically active component and a biodegradable carrier having a melting point of about 50° C. or less, more preferably about 45° C. or less. More particularly, the biodegradable carrier component has a melting point of from about 10° C. to about 50° C., more preferably from about 35° C. to about 45° C. In other specific embodiments, the invention provides a coated stent comprising a stent and a coating composition that includes a bioactive component and a biodegradable liquid carrier component having a viscosity of from about 0.1 to about 15,000 centipoise, and more preferably from about 0.1 to 5000 centipoise (cP). In yet another specific embodiment, the invention includes a stent with a coating composition that is in a solid state at room temperature (22° C.) outside a human body and that melts to form a liquid inside a human body.

In another embodiment, the coating composition comprises an effective amount of a non-polymeric carrier. In a particular embodiment, the non-polymeric carrier comprises a fatty acid. The non-polymeric carrier may alternatively comprise a biocompatible oil, wax, or gel. In a yet further embodiment, the non-polymeric carrier may comprise a mixture of one or more of a fatty acid, an oil, a wax, and/or a gel.

Coating compositions according to the present invention are preferably hydrophobic. More preferably, the biodegradable carrier component of the coating composition is hydrophobic. The carrier component is also preferably biocompatible. The biodegradable carrier may comprise a polymer. When the biodegradable carrier.

In another aspect, the invention can include a method of coating a stent. In a specific embodiment, the method includes providing a coating composition comprising a blend of a substantially unreacted HMG-CoA reductase inhibitor and a polymeric or nonpolymeric carrier, and applying the coating composition to the stent. Providing the coating composition may include mixing the HMG-CoA reductase inhibitor and a nonpolymeric liquid carrier. In one embodiment, the nonpolymeric liquid carrier comprises a C-6 to C-18 fatty acid. In another embodiment, providing the coating composition may include mixing the HMG-CoA reductase inhibitor and a polymeric liquid carrier. In a further embodiment, providing the coating composition may include mixing the HMG-CoA reductase inhibitor, a polymer, and a solvent under conditions such that the HMG-CoA reductase inhibitor does not chemically react with the polymer, or does not react to any substantial extent. Providing the coating composition may also include mixing the HMG-CoA reductase inhibitor, a polymer, and a solvent at a temperature of from about 20° C. to about 30° C., preferably at about 25° C. The method of coating the composition may further comprise removing the solvent by, e.g., drying. In another embodiment, providing a coating composition may include providing a solid coating comprising an HMG-CoA reductase inhibitor and a polymer.

In another specific embodiment, the invention includes a method that comprises providing a coating composition that includes a biologically active component and a biodegradable carrier component which has a viscosity of from about 0.1 to about 15,000 cP, and applying the coating composition to the stent.

In another embodiment, a method of coating a stent may further comprise expanding the stent to an expanded position before applying the coating composition to the stent. The coating composition may be applied to the stent by any number of ways, e.g., by spraying the coating composition onto the stent, by immersing the stent in the coating composition, or by painting the stent with the coating composition. Other coating methods, such as electrodeposition can also be used. In one embodiment, excess coating composition is allowed to drain from the stent. In another embodiment, the stent is dried after the coating composition is applied to the stent to provide a solid coating composition. The coating composition may be formed into a solid film that is then applied to the stent by wrapping the film around the stent. In preferred embodiments, the coating is applied with the bioactive component dissolved in the carrier component. In alternative embodiments, the carrier component may be applied to the stent and the bioactive component applied to the carrier. In another alternative embodiment, the bioactive component may be applied to the stent and the carrier component applied to the bioactive component.

In one or more specific embodiments, the invention can include a treatment method, comprising inserting a coated stent into a body lumen of a person, the coated stent comprising a stent and a coating composition comprising a biodegradable carrier component and a biologically active component, the biodegradable carrier component having a melting point of about 50° C. or less, more preferably 45° C. or less. In other specific embodiments, the coated stent provides a stent and a coating composition comprising a biodegradable carrier component and a biologically active component, the carrier component having a viscosity of from about 0.1 to about 15000 cP, or from about 0.1 to about 5000 cP. In yet another specific embodiment, the coated stent comprises a stent and a coating composition that comprises a biodegradable carrier component and a biologically active component, and the coating composition (or at least the carrier component thereof) is in a solid state outside of a human body and a liquid inside of a human body.

In another aspect, the invention can include a treatment method, comprising attaching a stent to a catheter, spraying the catheter and the stent with a coating composition comprising a biodegradable carrier component, and a biologically active component having a melting point of about 50° C. or less, and inserting the coated stent into a body lumen of a person.

In another aspect, the invention can include a coated stent, comprising a stent and a coating composition comprising a biologically active component and a biodegradable carrier component which may have a melting point of about 50° C. or less, and a catheter which can be coupled to the coated stent to form a treatment assembly.

In another aspect, the invention includes a method of treating an occluded artery comprising providing a stent, providing a coating composition comprising a nonpolymeric or polymeric carrier and a HMG-CoA reductase inhibitor in an amount effective to prevent or substantially reduce restenosis, applying the coating composition to the stent, and deploying the stent in the occluded artery at the site of occlusion. Providing a coating composition may comprise dissolving or suspending an amount of the HMG-CoA reductase inhibitor effective to prevent or substantially reduce restenosis in a nonpolymeric carrier that is a liquid at room and/or body temperature. In another embodiment, providing a coating composition may comprise dissolving in a polymeric carrier that is a liquid at room and/or body temperature an amount of the HMG-CoA reductase inhibitor effective to prevent or substantially reduce restenosis in an occluded vascular lumen. In alternative embodiments, the nonpolymeric or polymeric carrier may be a solid at room and body temperature. Where a polymeric carrier is provided, the HMG-CoA reductase inhibitor may be physically bound to the polymer, chemically bound to the polymer, or both. The coating composition may be a solution which includes the HMG-CoA reductase inhibitor, the polymer, and a solvent. The solvent may be removed by, e.g., drying the stent or other methods known in the art to yield a stent having a solid polymeric carrier for the HMC-CoA reductase inhibitor. The coating composition may include an amount of the HMG-CoA reductase inhibitor that is therapeutically effective for inhibiting regrowth of plaque or inhibiting restenosis. More particularly, the coating composition may include from about 1 wt % to about 50 wt % HMG-CoA reductase inhibitor, based on the total weight of the coating composition.

In another aspect, the invention can include a method of treating restenosis, comprising inserting a coated stent into a body lumen, the coated stent comprising a stent and a coating composition comprising a substantially unreacted HMG-CoA reductase inhibitor and a nonpolymeric or polymeric carrier, which may be a liquid at room and body temperature, a solid at room and body temperature, or a solid at room temperature and a liquid at body temperature. In one embodiment, the coated stent releases the HMG-CoA reductase inhibitor in an amount sufficient to inhibit or reduce the regrowth of plaque. In another embodiment, the coated stent releases the HMG-CoA reductase inhibitor in an amount sufficient to inhibit or reduce restenosis.

In another aspect, the invention can include a method of localized delivery of an HMG-CoA reductase inhibitor, comprising inserting a coated stent into a body lumen, the coated stent comprising a stent and a coating composition comprising a substantially unreacted HMG-CoA reductase inhibitor and a polymeric or nonpolymeric carrier. In one embodiment, the coated stent releases the HMG-CoA reductase inhibitor in an amount effective to inhibit the regrowth of plaque. In another embodiment, the coated stent releases the HMG-CoA reductase inhibitor in an amount effective to inhibit restenosis.

BRIEF DESCRIPTION OF THE DRAWINGS

FIG. 3 is a stent of a type suitable for use in connection with the present invention.

FIG. 4 is a UV-VIS spectra of cerivastatin released from a stent coating.

FIG. 5 is a release profile of cerivastatin released from a stent coating of EVA film.

FIG. 6 is a release profile of cerivastatin released from a stent coating of polycaprolactone film.

FIG. 7 is a release profile of cerivastatin released from a stent coated with silicone.

FIG. 8 is a release profile of cerivastatin released from a stent coated with liquid vitamin.

DETAILED DESCRIPTION OF THE PREFERRED EMBODIMENT

Figure 1:
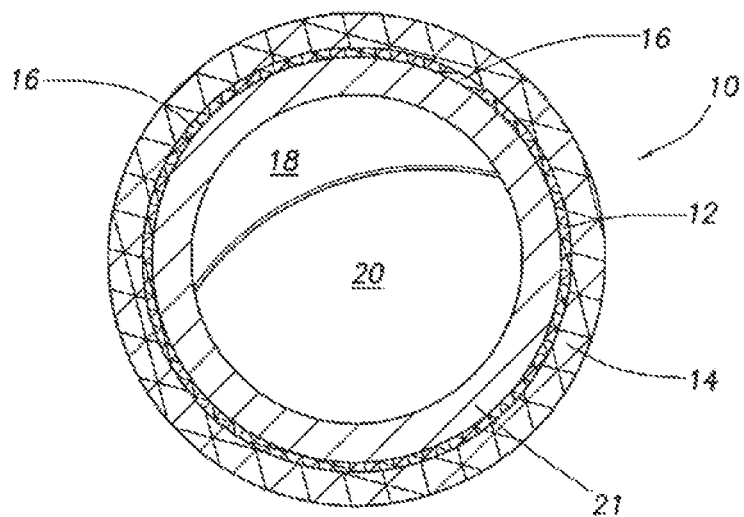
FIG. 1 is a cross-section of an artery experiencing restenosis in the presence of an uncoated stent.

An exemplary artery 10 experiencing restenosis is shown in FIG. 1. The endothelium 12 normally serves as a solid barrier between the layer of smooth muscle cells 14 and the arterial lumen 20. Small tears 16 in the endothelium 12 can expose smooth muscle cells 14, which can then migrate into the arterial lumen 20 and hyperproliferate into a mass 18 which can partially or completely occlude the lumen 20 even though an uncoated stent 21 is placed, during a procedure such as angioplasty, in the artery 10 to keep the arterial lumen 20 open.

Figure 2:
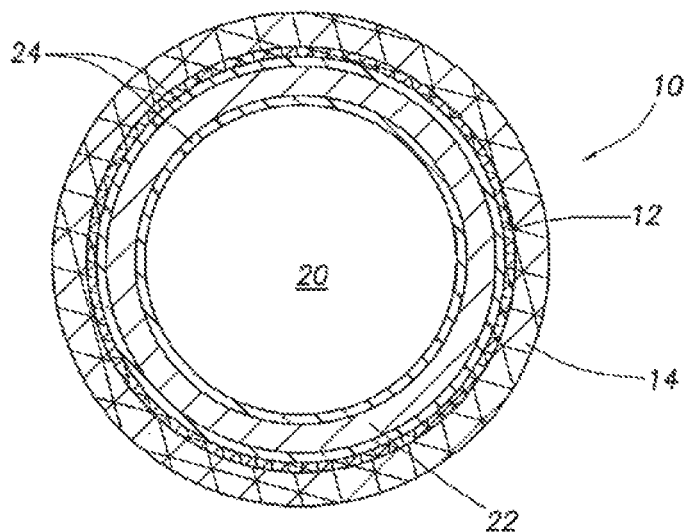
FIG. 2 is a cross-section of an artery containing a coated stent.

An artery 10 containing a coated stent 22 prepared according to an embodiment herein is shown in FIG. 2. The stent has a coating 24 containing a carrier and a bioactive compound that inhibits restenosis. By using a stent having this coating 24, the tears 16 shown in FIG. 1 in the endothelium 12 may be reduced or eliminated. Additionally, the mass 18 created by a proliferation of smooth muscle cells 14, as shown in FIG. 1, is eliminated or substantially reduced.

FIG. 3 illustrates a stent 21 suitable for use in connection with the present invention. In one embodiment, the stent 21 comprises a hollow reticulated tube. The tubular body of stent 21 is defined by a number of filaments or struts 25 which surround open cells 26. The stent 21 comprises an inner surface 27 facing the interior of the stent and an outer surface 28 facing the exterior. In a preferred embodiment, a coating (now shown) covers both the inner surface 27 and the outer surface 28. In alternative embodiments, the coating may cover only the inner surface, only the outer surface, or portions of one or both of the inner and outer surfaces. The coating may aggregate at the intersection of filaments. In a preferred embodiment, the coated stent 22 (FIG. 2) is made out of a metal or metal alloy, such as titanium, tantalum, stainless steel, or nitinol. In a preferred embodiment, the coating 24 is made by mixing together an HMG-CoA reductase inhibitor, and a carrier in which both the HMG-CoA reductase inhibitor is soluble. In a particularly preferred embodiment, the carrier is a liquid oil that adheres to the inner and outer surfaces 27, 28 of the stent 22. In other embodiments, the carrier comprises a polymer dissolved in a solvent, which is then removed, e.g., by drying, to yield a solid coating composition comprising the polymer and the HMG-CoA reductase inhibitor.

At least certain embodiments of the invention include a coated stent comprising a stent and a coating composition that includes a biologically active component and a biodegradable carrier component having a melting point of about 50° C. or less. Preferably, the biodegradable component has a melting point of from about 10° C. to about 50° C., and most preferably, from about 35° C. to about 45° C. In other specific embodiments, the invention provides a coated stent comprising a stent and a coating composition comprising a bioactive component and a liquid biodegradable carrier component that has a viscosity of from about 0.1 to about 15000 cP, and more preferably, from about 0.1 to about 5000 cP. In yet another specific embodiment, the invention includes a stent with a coating composition that is in a solid state at room temperature (22° C.) a human body and that melts to form a liquid inside a human body at body temperature (37° C.).

In a preferred embodiment, the coating 24 (FIG. 2) is made by mixing together a biologically active component (e.g., a restenosis-inhibiting agent) and a carrier in which the biologically active component is soluble. In a particularly preferred embodiment, the carrier is a liquid oil that adheres to the inner and outer surfaces 27, 28 of the stent 21 (FIG. 3). In other embodiments, the carrier comprises a low-melting polymer dissolved in a solvent, which is then removed by, e.g., drying, to yield a solid coating composition comprising the polymer and bioactive component, which may comprise a restenosis inhibiting agent such as an HMG-CoA reductase inhibitor.

As discussed, the coated stent of this invention includes a stent and a coating composition. The coating composition is preferably a blend of a biologically active component, e.g., an HMG CoA reductase inhibitor and a liquid oil capable of adhering to the inner surface 27 and/or the outer surface 28 of the stent 22. In another embodiment, the coating composition comprises a blend of HMG-CoA reductase inhibitor and a polymer. These two ingredients are preferably blended, e.g., mixed thoroughly but not chemically reacted to any substantial degree. Preferably the HMG-CoA reductase inhibitor is "substantially unreacted." The term "substantially unreacted," when referring to the HMG-CoA reductase inhibitor, means that the inhibitor does not chemically react with the oil, the polymer or any other component of the coating or the stent, to any degree that substantially reduces its biological activity, such as inhibiting restenosis by, e.g., inhibiting the proliferation of smooth muscle cells 14. Where the coating comprises a polymer, the reductase inhibitor is physically bound to the polymer and/or to the stent, but is not chemically bound to any significant degree. In a preferred embodiment, the carrier, whether liquid or solid, polymeric or nonpolymeric, is incapable of reacting chemically with the inhibitor, i.e., is totally non-reactive (inert) with respect to the inhibitor.

In another embodiment the coating composition described herein is preferably a blend of a biologically active component and a biodegradable low-melting carrier component. The terms "biologically active" and "bioactive" refer to a substance having an effect on a living organism. See generally, Merriam Webster's Collegiate Dictionary (10$^{th}$ ed., 2001). Preferably, the effect of a bioactive compound is therapeutic in nature. The term "biodegradable" as used herein refers to a substance that breaks down into non-toxic byproducts which are eliminated by the body. The term "low-melting" refers to a composition having a melting point of 50° C. or less. Carrier compositions having melting points below 50° C. allow liquid-form delivery of a bioactive component to a body lumen either with no heat at all (because the composition is a liquid at body temperature) or with relatively benign heating without denaturing or other harm to the patient. In another embodiment, the coating composition is a blend of a bioactive component and a low-melting carrier comprising a biodegradable component, a biostable component, or both. In yet another embodiment, the coating composition is a liquid carrier that is biodegradable or biostable.

An important aspect of the coating compositions of the present invention is the melting point of the biodegradable component. Preferably, the biodegradable component has a melting point of 50° C. or less, and more preferably from about 35° C. to about 45° C. The term "melting point" refers generally to the temperature at which a pure substance's crystals are in equilibrium with the liquid phase at atmospheric pressure. See generally, Hawley's Condensed Chemical Dictionary (11$^{th}$ Ed., 1987). Whenever melting points are discussed or referred to herein in quantitative terms, the melting point is measured according to differential scanning calorimetry or other standard methods shown in analytical or organic chemistry textbooks (see, e.g., Analytical Chemistry Handbook, Section 15, J. A. Dean, McGraw-Hill, Inc., 1995).

Another important aspect of certain embodiments of the invention is the biodegradable carrier component. In a preferred embodiment of this invention, the carrier component of the coating composition is or includes one or more non-polymeric, biodegradable compounds or materials, which either contain no polymers at all or contain essentially no polymers. For example, the carrier component should contain less than 50% by weight polymer, preferably less than 25 wt % polymer, more preferably less than 10 wt %, and most preferably less than 1 wt % polymer material. The biodegradable carrier component is preferably homogeneous (single phase) and may comprise a mixture of components that exist together as a solution, but which may alternatively be a multiple phase blend. Examples of preferred non-polymeric biodegradable carriers include liquid oleic acid, vitamin E, peanut oil, and cottonseed oil, which are liquids that are both hydrophobic and biocompatible.

The biologically active component, e.g., an HMG-CoA reductase inhibitor, should remain active even after being coupled to the carrier to form the coating composition and even after the coating composition is applied to the stent and the device is sterilized. Preferably, the bioactive component remains active when the coated stent is introduced into the body of a patient, e.g., through a lumen, and is also still active when it is released from the stent. An "effective amount" of the HMG-CoA reductase inhibitor means an amount that is sufficient, when delivered to a localized area in the body lumen of a patient, to inhibit the proliferation of smooth muscle cells in a body lumen of a patient. An "effective amount" of the carrier means an amount of carrier sufficient to dissolve or suspend an effective amount of the bioactive component, and to provide an amount of the coating composition to substantially coat the portion of the stent that is desired to be coated, preferably the entire stent. Preferably, the carrier has no functional groups that react with the bioactive component, e.g., an HMG-CoA reductase inhibitor, under the conditions of forming the blend of the HMG-CoA reductase inhibitor and the carrier. The term "biodegradable" is applied herein to any carrier, whether polymeric or nonpolymeric, and whether liquid or solid, that breaks down in the body. The term "biostable" is applied herein to any carrier, whether polymeric or nonpolymeric, and whether liquid or solid, that does not break down in the body. The term "biocompatible" describes any material that is not harmful to and does not cause an immunological response in a body, e.g., a human being.

In accordance with methods and compositions described herein, restenosis may be prevented or lessened using localized delivery of HMG-CoA reductase inhibitors from a stent placed in a body lumen. Preferably, metal stents are coated with a biocompatible coating composition comprising a carrier containing an effective amount of an HMG-CoA reductase inhibitor. The coated stent can be deployed during any conventional percutaneous transluminal angioplasty (PTA) procedure. Controlled delivery from a stent of the active HMG-CoA reductase inhibitor, using a stent such as that described herein, in an effective amount, can inhibit the regrowth of plaque and prevent restenosis. While the stents shown and described in the various embodiments are vascular stents, any type of stent suitable for deployment in a body lumen of a patient may be used with the coatings described herein.

An important aspect of this invention is the carrier used to form the coating composition. The coating composition may comprise more than one compound in a liquid carrier. The coating composition may alternatively comprise more than one solid compound in a solid carrier. The coating composition may further comprise both a liquid carrier and a solid carrier. In a still further aspect, the coating composition may also comprise more than one type of nonpolymeric or polymeric compound in the carrier, and may further comprise both a polymeric material and a nonpolymeric material in a solid or liquid carrier. In a yet further aspect of the invention, the coating composition may comprise more than one type of HMG-CoA reductase inhibitor. In coatings created by this method, the HMG-CoA reductase inhibitors are preferably physically bound to the carrier but not chemically bound thereto. Accordingly, the chemical or molecular structure of the HMG-CoA reductase inhibitor is preferably unchanged when they are mixed with the polymers to form the coating. Therefore, when the HMG-CoA reductase inhibitor is released from the coating, it remains in the desired active form.

As used herein, the terms "liquid" and "solid" are defined according to their broadest recognized definitions. Unless stated otherwise, a material is determined to be a "liquid" or "solid" at room temperature, i.e., 22° C. The term "liquid," when referring to carriers and coating compositions according to the present invention, includes a fluid (as water) that has no independent shape but has a definite volume, does not expand indefinitely and is only slightly compressible. The term "liquid" also includes any amorphous (e.g., noncrystalline) form of matter intermediate between gases and solids in which the molecules are much more highly concentrated than in gases but much less concentrated than in solids. See, generally, Hawley's Condensed Chemical Dictionary, ($11^{th}$ Ed., 1987). As discussed in further detail below, an amorphous liquid having a high viscosity can be used to advantage in compositions according to the present invention. The term "solid," when referring to carriers and coating compositions, includes a substance that does not flow perceptibly under moderate stress, has a definite capacity for resisting forces (e.g., compression or tension) which tend to deform it, and, under ordinary conditions, retains a definite size and shape. See generally, Merriam Webster's Collegiate Dictionary ($10^{th}$ ed., 2001).

The coating composition, including the bioactive component and the carrier, should be non-fragmentary. That is, the coating composition preferably does not break down into solid, potentially harmful fragments when the coated stent is in the body. In certain embodiments, the biodegradable carrier is a liquid when it is part of the coating composition residing on the stent outside the body. This liquid is incapable of breaking down into solid, potentially harmful fragments. In other embodiments, the biodegradable carrier is a solid that preferably becomes a liquid when introduced to the body (or shortly thereafter). For example, the carrier can be a solid at typical ambient temperatures (i.e., from 20° C. to 30° C.), and is preferably a solid at about 22° C., i.e., room temperature. It should, however, become a liquid at the temperature of a human body, which is approximately 37° C. In other words, the biodegradable component may be a solid outside a human body and a liquid inside a human body, so that it melts to form a liquid when inside the body. It is also contemplated that one skilled in the art may blend a biodegradable compound which is solid at typical ambient temperatures (or room temperature) with other components to form a carrier which can be either a liquid at ambient temperatures (or room temperature) or a liquid at the temperature of a human body.

In yet a further embodiment of the present invention the coating composition comprises a nonpolymeric compound that is a solid at room temperature but becomes a liquid at or near body temperature. In particular, the coating composition comprises low molecular weight waxes and derivatives having a melting point at between about 30° C. and 40° C., more particularly from about 35° C. to 40° C. and more particularly about 36° C. to about 38° C. In preferred embodiments, the low melting solid is applied to the stent by heating the solid to above its melting point, then sprayed, painted, dipped, molded, or otherwise applied to the stent as a liquid and allowing the liquid to resolidify upon cooling at ambient temperatures.

In another embodiment, two or more types of biodegradable compounds (polymers or non-polymers) may be blended together to obtain a liquid carrier for use in the coating composition. The biodegradable compounds can be liquids before they are mixed together, e.g., forming a homogeneous solution, mixture, or suspension. Alternatively, some of the biodegradable compounds may be solids before they are mixed with other liquid biodegradable compounds. The solid biodegradable compounds preferably dissolve when they are mixed with the liquid biodegradable compounds, resulting in a liquid carrier composition containing the different biodegradable compounds. In another embodiment, the biodegradable carrier component of the coating composition is a solid, which dissolves when mixed with the biologically active component and any other components included in the coating composition.

In certain specific embodiments, an important aspect of the biodegradable carrier component is its viscosity. Generally, viscosity is a term that refers to thickness or resistance to flow. In quantitative terms, the biodegradable component should have a viscosity of from about 0.1 to about 15000 cP. A person skilled in the polymer chemistry art can use Brookfield viscometer to measure viscosity of variety of fluids. Whenever viscosity is discussed herein in quantitative terms, the term "viscosity" is defined according to an ASTM method describing viscosity measurement can be found in Test Method D2983-87 entitled "Standard Test Method for Low-Temperature Viscosity of Automotive Fluid Lubricants Measured by Brookfield Viscometer."

Preferably, liquid stent coatings, such as those made from the materials described herein, have sufficient viscosity to withstand blood and other body fluids flowing against them without being washed off a stent, both during the insertion of the stent into the body and after the implantation of the stent at the desired site. Accordingly, in a preferred embodiment, the biodegradable carrier is a highly viscous liquid, e.g., an amorphous or even a "slimy" material that forms a liquid coating on the stent. A viscosity of from about 0.2 to about 200 cP is preferred. Preferably, the viscosity of the biodegradable carrier results in a coating that is less likely to be removed from the stent by the shear forces created by blood flow past the stent than a coating including a biodegradable carrier having a lower viscosity. The various viscosities discussed herein are measured at 20° C.

In order to create coatings in which HMG-CoA reductase inhibitors are physically rather than chemically bound to the polymers in the coatings, HMG-CoA reductase inhibitors and carriers are chosen such that they will not have functional groups that will react with each other under the compounding conditions of to form the coating solution.

The carriers in the coating composition may be either biodegradable or biostable. Biodegradable polymers are often used in synthetic biodegradable sutures. These polymers include polyhydroxy acids. Polyhydroxy acids suitable for use in the present invention include poly-L-lactic acids, poly-DL-lactic acids, polyglycolic acids, polylactides including homopolymers and copolymers of lactide (including lactides made from all stereo isomers of lactic acids, such as D-, L-lactic acid and meso lactic acid), polylactones, polycaprolactones, polyglycolides, polyparadioxanone, poly 1,4-dioxepan-2-one, poly 1,5-dioxepan-2-one, poly 6,6-dimethyl-1, 4-dioxan-2-one, polyhydroxyvalerate, polyhydroxybuterate, polytrimethylene carbonate polymers, and blends of the foregoing. Polylactones suitable for use in the present invention include polycaprolactones such as poly(e-caprolactone), polyvalerolactones such as poly(d-valerolactone), and polybutyrolactones such as poly(?-butyrolactone). Other biodegradable polymers that can be used are polyanhydrides, polyphosphazenes, biodegradable polyamides such as synthetic polypeptides such as polylysine and polyaspartic acid, polyalkylene oxalates, polyorthoesters, polyphosphoesters, and polyorthocarbonates. Copolymers and blends of any of the listed polymers may be used. Polymer names that are identical except for the presence or absence of brackets represent the same polymers.

Biostable polymers that are preferred are biocompatible. Biostable polymers suitable for use in the present invention include, but are not limited to polyurethanes, silicones such as polyalkyl siloxanes such as polydimethyl siloxane and copolymers, acrylates such as polymethyl methacrylate and polybutyl methacrylate, polyesters such as poly(ethylene terephthalate), polyalkylene oxides such as polyethylene oxide or polyethylene glycol, polyalcohols such as polyvinyl alcohols and polyethylene glycols, polyolefins such as polyethylene, polypropylene, poly(ethylene-propylene) rubber and natural rubber, polyvinyl chloride, cellulose and modified cellulose derivatives such as rayon, rayon-triacetate, cellulose acetate, cellulose acetate butyrate, cellophane, cellulose nitrate, cellulose propionate, cellulose ethers such as carboxymethyl cellulose and hydroxyalkyl celluloses, fluorinated polymers such as polytetrafluoroethylene (Teflon), and biostable polyamides such as Nylon 66 and polycaprolactam. Fixed animal tissues such as glutaraldehyde fixed bovine pericardium can also be used. Polyesters and polyamides can be either biodegradable or biostable. Ester and amide bonds are susceptible to hydrolysis, which can contribute to biodegradation. However, access to water, and thus, hydrolysis, can be prevented by choosing certain neighboring chemical structures.

In a preferred embodiment, the polymer used to form the coating composition is polycaprolactone. Polycaprolactone is biocompatible, and it has a low glass transition temperature, which gives it flexibly and allows it to withstand the temperature changes stents often experience during their formation and use. For example, nitinol stents are preferably cooled to a temperature of about −50° C. so that they become flexible and can be compressed and fitted onto a catheter. A sheath placed over the stent (or another restraint such as a wire binding the ends of the stent), prevents the stent from expanding as it is introduced into a patient's body at a higher temperature. The sheath or other restraint is removed at the site of the stent's use, and the stent re-expands to the size at which it is coated with a composition that includes polycaprolactone. Polycaprolactone, unlike some other stent coating materials, does not become brittle and crack throughout these fluctuations in stent temperature and size. Preferably, the polycaprolactone has a molecular weight between about 20,000 and 2,000,000, and provides a stronger and more uniform coating than lower molecular weight polymers.

Generally, the bioactive component, e.g., an HMG-CoA reductase inhibitor is released from the stent by diffusion of the HMG-CoA reductase inhibitor out of the carrier. If the carrier comprises a biodegradable polymer, the bioactive component is preferably released from the stent by the degradation of the polymer. A controlled release of the bioactive component from the coating can be achieved with a carrier comprising both a liquid and a solid through the relatively rapid release of the diffusion of the bioactive component from the liquid and a slower release from the solid. In a still further embodiment, a highly controlled delivery of the bioactive component can be achieved by a carrier comprising a liquid, a biodegradable (preferably solid) polymer, and a biostable (preferably solid) polymer. An initial release of the bioactive component from the liquid may be followed by a slower release from the biodegradable solid, and a still slower release from the biostable solid.

The diffusion rate of the bioactive component, e.g. an HMG-CoA reductase inhibitor, from the carrier can be determined by release studies and the dose can be adjusted to deliver the drug at a desired rate. In one embodiment, a higher dose of the bioactive component can be delivered over a short period of time by using a liquid that releases a known amount of the inhibitor within one to three days. In another embodiment, a higher dose of bioactive component can be delivered over a short period of time by using a nonpolymeric liquid carrier such as vitamin E. In another embodiment, the bioactive component can be delivered via a biodegradable polymer that degrades within a few days, e.g., low molecular weight polyglycolic acid, releasing the bioactive component by both diffusion and/or coating degradation. In another embodiment, a biodegradable polymer which delivers an HMG CoA reductase inhibitor primarily through diffusion is used. An example of such a polymer is polycaprolactone, which degrades after several years in the body. In another embodiment, the carrier may comprise a nonpolymeric liquid and a biodegradable polymer that is a solid at room temperature ad a liquid at body temperature.

Advantageously, the rate of release of a bioactive component from a liquid coating can be more easily predicted and is more consistent than the rate of release of a drug from other coatings in which the drug is chemically bound to the coating. With the coatings described herein, the bioactive component(s) are preferably physically released from the coatings, and thus, not dependent on a chemical step, such as hydrolysis, whose rate could vary in different patients as well as within the same patient.

In at least certain embodiments the coating compositions of the present invention release their biologically active components in the body both by diffusion of the bioactive compounds from the coatings and by degradation of the coatings. For coating compositions that degrade within a few days or weeks in the body, much of the release of the biologically active components occurs in this time frame. This time-release feature is advantageous because it is believed that a high dose of a biologically active component, such as an antirestenosis compound or an antibiotic, delivered quickly can often be more effective than a lower dose delivered over a longer period of time. For example, bacterial infections are often treated with high doses of antibiotics as soon as the infection is detected. A high initial dose of antibiotics may kill all of the bacteria, whereas a lower dose of antibiotics administered over a longer period of time often results in the selection for, and survival of, bacteria that can survive in the presence of a low dose of the drug. Similarly, it is contemplated that if a low concentration of a biologically active component, such as a restenosis inhibitor which inhibits smooth muscle cell proliferation, is released slowly from a stent, some smooth muscle cells will still be able to proliferate and partially occlude the artery. Then, when the supply of the biologically active component is exhausted, this small group of smooth muscle cells will continue to proliferate and block a larger percentage of the arterial lumen. It is contemplated that this situation can be avoided or minimized using coating compositions described herein, because it is believed that the liquid coatings will be removed from the stent and degraded within a few days or weeks, and thus deliver a localized, high dose of a biologically active component in a short period of time.

The liquid coating compositions described herein which are made from biodegradable materials will degrade in the body and be removed from the angioplasty balloon or stent. When these coating compositions degrade, they typically degrade into their molecular subunits without creating fragments that may irritate or damage the endothelium and lead to restenosis, possibly in areas remote from the site of stent deployment. Thus, these coating compositions provide safe, temporary coatings for stents. Also, the coatings typically provide a smooth surface for stents, which minimizes abrasion or tearing damage to the endothelium by stents during and after their implantation in the body. It is contemplated that minimizing damage to the endothelium minimizes the likelihood of the development of restenosis. The coating compositions may also protect the stent itself from chemical or physical damage in the body.

The coating composition comprising the carrier and the HMG-CoA reductase inhibitor can be applied to a stent in a number of different ways. Preferably, a stent is coated in its expanded form so that a sufficient amount of coating will be applied to coat the expanded stent. In a preferred embodiment, the coating composition is at least initially applied to the stent as a liquid. Spraying the stent with the liquid carrier results in a coating of uniform thickness on the struts of the stent. Where the coating composition comprises a solid polymer, the polymer is preferably dissolved in a suitable solvent to form a polymer solution and the stent is sprayed with the solution in order to coat the stent struts. Alternatively, the polymer solution may be painted on the stent or applied by other means known in the art, such as electrodeposition, dipping, casting or molding. The solvent may then be dried to yield a solid coating composition comprising the polymer. In one embodiment, the stent may be dip coated or immersed in the solution, such that the solution completely coats the struts of the stent. In each of these coating applications, the entirety of both the outer and inner surfaces of the stent are preferably coated, although only portions of either or both surfaces may be coated in alternative embodiments. In one embodiment, excess coating composition is allowed to drain from the stent. In another embodiment, the solvent may then be dried to yield a solid coating composition having a melting point of 50° C. or less, preferably at body temperature or less. In a preferred embodiment, the stent is dried at from 20° C. to 30° C. or ambient temperature for a period of time sufficient to remove the solvent. The drying temperature should not be high as to cause the polymer to react chemically with the HMG-CoA reductase inhibitor.

Multiple layers of the polymer solution may be applied to the stent. Preferably, each layer is allowed to dry before the next coating is applied. While an HMG-CoA reductase inhibitor is included in at least one layer of the coating, the coating solution in the other layers may optionally also contain the same or a different HMG-CoA reductase inhibitor. The polymer solution for each layer may contain the same or different polymers. The number of layers and the polymers in the layers can be chosen to deliver an HMG-CoA reductase inhibitor in a controlled manner because the rate of diffusion of the HMG-CoA reductase inhibitor through a known thickness of polymers can be estimated or measured directly.

In one embodiment, a first layer of the polymer solution, e.g., a primer layer, may be applied to improve the adhesion of the coating composition to the stent surface. Generally, coating a stent by completely encapsulating the struts of the stent is preferred. Complete encapsulation typically provides uniform distribution of a drug along the surfaces of the stent. A completely encapsulated coated stent is also more resistant than a partially coated stent to peeling and other mechanical stresses encountered during stent deployment. In certain specific embodiments, a top layer of the polymer solution without a drug may be applied on the coating. The top coating may be used to control the diffusion of the drug from the stent. The thickness of the coating is preferably 0.1 microns to 2 mm, more preferably from 1 to 100 microns, even more preferably from 1 to 25 microns. More preferably, the thickness of the coating is from 1 to 50 microns. Most preferably, the thickness of the coating is from 10 to 30 microns. However, to provide additional coating to effect release of higher doses of the bioactive component, grooves, capillaries, channels or other depressions in the surface of the stent or struts may be provided to increase the surface area and thereby provide sites of enhanced adhesion of the coating.

Specific embodiments of the invention include a stent with multiple coatings or layers, e.g., films. For example, a stent with three or more coatings or layers can be provided, where the first layer (contacting the stent) comprises a first carrier material having substantially no HMG-CoA reductase inhibitor, the second layer (applied to the outer surface of the first layer) includes the HMG-CoA reductase inhibitor in a second carrier material, and the third layer (applied to the second layer) comprises a third carrier material having substantially no HMG-CoA reductase inhibitor.

In another embodiment, the polymer solution can be formed into a film and the film then applied to the stent. Any of a variety of conventional methods of forming films can be used. For example, the polymer, HMG-CoA reductase inhibitor and solvent are preferably mixed into solution and then poured onto a smooth, flat surface such that a coating film is formed after the solution is dried to remove the solvent. The film can then be cut to fit the stent on which it is to be used. The film may then be mounted, such as by wrapping, on the outer surface of a stent.

As used herein, the term "solvent" is defined according to its broadest recognized definition and includes any material into which the carrier and/or the bioactive agent, e.g. the polymer and the HMG-CoA reductase inhibitor can dissolve, fully or partially, at room temperature or from 20° C. to 50° C. or from 20° C. to 40° C. Methylene chloride is a preferred solvent. Methylene chloride's low boiling point facilitates removal from the polymer and the HMG-CoA reductase inhibitor at ambient temperatures by evaporation. However, it is contemplated that virtually any organic solvent that dissolves the polymer can be used. Solvents that can cause corrosion, such as highly acidic or basic aqueous solutions, are not preferred. Organic solvents that are biocompatible, have low boiling points and high flash points, are preferred. Other solvents that may be used include chloroform, toluene, cyclohexane, acetone, methylethyl ketone, ethyl formate, ethyl acetate, acetonitrile, n-methyl pyrrolidinone, dimethyl sulfoxide, n,n-dimethylacetamide, n,n-dimethyl formamide, ethanol, methanol, acetic acid, and supercritical carbon dioxide.

In a particularly preferred embodiment, the coating composition comprises a nonpolymeric liquid that remains a liquid after it is applied to the stent and the stent is deployed within the body of a patient, i.e., the coating liquid has a melting point below body temperature (37° C.), preferably below 30° C., more preferably below room temperature (22° C.), more preferably below 20° C., still more preferably below 10° C. The liquid is preferably a viscous liquid that adheres to at least a portion of the external surface 28 of the stent 22 in sufficient quantity to deliver a therapeutically effective amount of the HMG-CoA reductase inhibitor upon expansion in the body of the patient. Although the viscous liquid may be hydrophilic, in a preferred embodiment the viscous liquid is hydrophobic. Specifically, the carrier may comprise liquid Vitamin E and derivatives thereof, such as vitamin E acetate and vitamin E succinate.

Biodegradable carriers and coating compositions according to the present invention are preferably hydrophobic so that the coating composition is not immediately dissolved and washed off the stent in the aqueous environment of the body. Hydrophilic and water-soluble biodegradable carriers and coating compositions may in some cases be used, but they are less preferred because of their tendency to be dissolved and washed off the stent more quickly than hydrophobic and water-insoluble biodegradable carriers and coating compositions. The term "hydrophobic" is defined according to its broadest recognized definition, and includes being antagonistic to water, and incapable of dissolving, or having limited solubility, in water. See generally, Hawley's Condensed Chemical Dictionary (11$^{th}$ Ed., 1987).

In another preferred embodiment, the viscous, hydrophobic liquid comprises a C4-C36 fatty acid or mixtures of such fatty acids, such as oleic acid or stearic acid, by way of nonlimiting example. In yet another preferred embodiment, the viscous, hydrophobic liquid comprises an oil. Exemplary oils suitable for use in the present invention include peanut oil, cottonseed oil, mineral oil, low molecular weight (C4-C36), and other viscous organic compounds that behave as oils such as, by way of nonlimiting example, 1,2 octanediol and other low molecular weight alcohols and polyols. Olive oil has a viscosity of 84 cP at 20° C. The viscosity of other materials is shown in Table 2 for reference purposes.

TABLE 2

| Viscosity of various materials at 20° C. | |
|---|---|
| Substance Name | Viscosity (Centipoise) |
| Water | 1 |
| Castor oil | 986 |
| Nylon resin melt | 100000 |
| Diethyl ether | 0.23 |
| Olive oil | 84 |
| Benzene | 0.65 |

Spraying the stent with the liquid carrier results in a coating of uniform thickness on the struts of the stent. In another embodiment, the stent may be dip coated or immersed in the solution, such that the solution completely coats the struts of the stent. Alternatively, the stent may be painted with the solution, such as with a paint brush. In each of these coating applications, the entirety of both the outer and inner surfaces of the stent are preferably coated, although only portions of either or both surfaces may be coated in some embodiments.

In yet a further embodiment of the present invention the coating composition comprises a nonpolymeric compound that is a solid at room temperature but becomes a liquid at or near body temperature. In particular, the coating composition comprises low molecular weight waxes and derivatives having a melting point at between about 30° C. and 40° C., more particularly from about 35° C. to 40° C. and more particularly about 36° C. to about 38° C. In preferred embodiments, the low melting solid is applied to the stent by heating the solid to above its melting point, then sprayed, painted, dipped, molded, or otherwise applied to the stent as a liquid and allowing the liquid to resolidify upon cooling. The stent may then be deployed in the body lumen, whereupon the coating composition re-liquifies.

An important aspect of certain embodiments of the invention is the biologically active component. One or more biologically active components are included in the coating composition; preferably before the coating composition is applied to a stent. It is, however, contemplated that the biologically active component may in certain cases be combined with the carrier to form the coating composition after the biodegradable component is applied to the stent. As discussed above, the coated stent may be used to deliver a bioactive material to a localized area in a body. Preferably, the biologically active component is one that inhibits restenosis and/or prevents smooth muscle cell proliferation. Preferred examples of biologically active components are components that inhibit cell growth by affecting one of the steps involved in the cell cycle. Preferred components that affect the cell cycle are anticancer agents such as paclitaxel, immunosuppressant compounds such as rapamycin, antibiotics such as actinomycin D, and HMG-CoA reductase inhibitors such as cerivastatin. Other bioactive components forming part of the coating composition can include compounds such as antithrombin agents such as heparin and hirudin, calcium channel blockers such as colchicine, and compounds that promote endothelialization such as nitric oxide or nicotine. In a preferred embodiment, the biologically active component is hydrophobic and is easily dissolved in the biodegradable carrier to form a hydrophobic liquid coating composition. It is particularly preferred that the hydrophobic biologically active component(s) have a low molecular weight, i.e., a molecular weight below 2000, and more preferably below 1000, which can be used to administer a localized treatment in the area of stent deployment. The treatment may be for a condition such as restenosis.

In embodiments in which a biologically active component is included in the coating composition, the biologically active component itself may be a liquid. For example, vitamin E and nicotine (free base) are liquid at ambient temperatures (see Table 1) and may potentially have an anti-restenosis therapeutic effect. Preferably, the liquid biologically active component is biodegradable. In certain embodiments, the coating composition may consist essentially of the biologically active component, without a separate carrier component. In certain embodiments, the coating composition may consist of the biologically active component.

TABLE 1

Bioactive compounds that are liquid or low melting solids (Sigma-Aldrich 2000 catalog)

| Substance Name | Molecular weight (Dalton) | Molecular formula | Physicsal appearance at ambient temperature |
|---|---|---|---|
| Vitamin E | 431 | $C_{29}H_{50}O_2$ | Liquid |
| Vitamin E acetate | 473 | $C_{31}H_{52}O_3$ | Liquid |
| Nicotine | 162 | $C_{10}H_{14}N_2$ | Liquid |
| Nicotine Hemisulfate Salt | 212 | $C_{10}H_{14}N_2 \cdot 1/2H_2SO_4$ | Liquid |

As discussed above, the coating composition comprises a bioactive component and a biodegradable carrier component. Preferably, the coating composition comprises from 0.1% to 100% by weight of a biologically active component and from 1% to 99% by weight of a biodegradable carrier component. More preferably, the coating composition comprises from 0.1% to 50% by weight of a biologically active component and from 50% to 99.9% by weight of a biodegradable carrier component. The coating composition can be prepared in a number of ways including by simply mixing the bioactive component and the carrier component together to form a mixture, e.g., a solution or suspension. Alternatively, the bioactive component and the carrier component together are mixed in a suitable solvent, the coating is applied to the stent, and the solvent is removed. Preferably the coating composition is applied to the stent in its expanded state.

Where a biologically active component is included in or on the coating composition, the biologically active component may compromise an HMG-CoA reductase inhibitor. In certain specific embodiments, a coated stent can comprise a stent and a coating composition comprising a substantially unreacted HMG-CoA reductase inhibitor and a carrier. The carrier in the coating composition may be either biodegradable or biostable.

In one embodiment, the coating composition comprises a blend of an HMG-CoA reductase inhibitor and a liquid oil, which may be nonpolymeric or polymeric, capable of adhering to the inner surface 27 and/or the outer surface 28 of a stent 21 as shown in FIG. 3. In another embodiment, the coating composition comprises a blend of an HMG-CoA reductase inhibitor and a polymer. These two ingredients are preferably blended, e.g., mixed thoroughly but not chemically reacted to any substantial degree. Preferably the HMG-CoA reductase inhibitor is substantially unreacted. The term "substantially unreacted," when referring to the HMG-CoA reductase inhibitor, means that the inhibitor does not chemically react with the oil, the polymer or any other component of the coating or the stent, to any degree that substantially reduces its biological activity, such as inhibiting restenosis, e.g., by inhibiting the proliferation of smooth muscle cells 14. Where the coating comprises a polymer, the reductase inhibitor is preferably physically bound to the polymer and/or to the stent, but not chemically bound to any significant degree. In a preferred embodiment, the carrier, whether liquid or solid, polymeric or nonpolymeric, is incapable of reacting chemically with the inhibitor, i.e., is totally non-reactive (inert) with respect to the inhibitor.

In a preferred embodiment, the HMG-CoA reductase inhibitor used in the coating composition is cerivastatin. Cerivastatin is a very potent HMG-CoA reductase inhibitor. For example, when it is administered systemically, a therapeutic dose of cerivastatin is less than 1 mg per day, while other HMG-CoA reductase inhibitors must be administered in 50 mg doses. A thinner stent coating can be used if cerivastatin is the chosen HMG-CoA reductase inhibitor instead of other HMG-CoA reductase inhibitors because less coating is needed. For example, a stent coating preferably has a thickness of about 10-100 µm. If less drug and less coating to carry the drug are required, a stent coating having a preferable thickness of 10-25 µm can be used. A thinner stent coating may be preferred because it leaves more of the arterial lumen open for blood flow. Thinner coatings are also useful in preserving sidebranch access. Sidebranches are small blood vessels that branch out from the coronary artery and provide blood to some part of the heart.

Cerivastatin has other properties, in addition to its ability to inhibit the proliferation of smooth muscle cells that can contribute to restenosis, making it a desirable component of stent coatings. For example, cerivastatin has anti-thrombotic activity. Stents can often be sites of thrombus formation in the body because of the immunologically-triggered aggregation of different cell types and blood components at the site of a foreign object in the body. Thus, including cerivastatin in a stent coating may help prevent thrombus formation at the site of the stent. Cerivastatin also promotes endothelialization, or the repair of the endothelium 12 after it is damaged, such as by the delivery and expansion of the stent in an artery or other body lumen. It is contemplated that the endothelialization triggered by cerivastatin can help repair the endothelium, and thus reduce tears in the endothelium through which smooth muscle cells and other cell types can migrate into the arterial lumen and proliferate, leading to restenosis.

Other HMG-CoA reductase inhibitors may be used in these stent coatings. For example, atorvastatin, simvastatin, fluvastatin, lovastatin, and pravastatin may be used. While these compounds are known for their antihypercholesterolemic properties, it is believed that they may have other beneficial activities, such as restenosis inhibition or inhibition of cell proliferation, when they are delivered in a localized manner, such as from a stent coating.

In one embodiment, the coating compositions described herein may include more than one bioactive component, preferably more than one type of HMG-CoA reductase inhibitor. For example, a coating composition may include cerivastatin and lovastatin. In other specific embodiments, the stent coatings described herein may include one or more drugs or bioactive compounds that inhibit restenosis and are not HMG-CoA reductase inhibitors. These drugs include, but are not limited to, rapamycin, paclitaxel, actinomycin D, nicotine, and bioactive derivatives, analogues, and truncates of the foregoing. It is contemplated that combining these drugs with an HMG-CoA reductase inhibitor will provide a more effective coating composition for inhibiting restenosis than a coating composition containing only one restenosis inhibiting agent. However, the foregoing may also be used without an HMG-CoA reductase inhibitor.

In addition to stents, examples of other medical devices that can be coated in accordance with aspects of the inventions disclosed herein include catheters, heart valves, pacemaker leads, annuloplasty rings and other medical implants. In other specific embodiments, coated angioplasty balloons and other coated medical devices can also comprise one of the coating compositions disclosed herein. However, stents are preferred. The coating composition may be applied to the stent (or other medical device) by any number of ways, e.g, by spraying the coating composition onto the stent, by immersing the stent in the coating composition, or by painting the stent with the coating composition. Preferably, a stent is coated in its expanded (i.e., enlarged diameter) form so that a sufficient amount of the coating composition will be applied to coat the entire surface of the expanded stent. When the stent is immersed in the coating composition, the excess coating composition on the surface of the stent may be removed, such as by brushing off the excess coating composition with a paint brush. In each of these coating applications, preferably both the outer and inner surfaces of the stent are coated.

The coatings of the present invention are suitable for use on any known cardiovascular stent such as, e.g., the Palmaz stent disclosed in U.S. Pat. Nos. 4,733,665 and 4,739,762. Other stents may also be used. Notwithstanding the foregoing, in a preferred embodiment, the coating compositions described herein are used on stents having struts, and further including a surface enhancing feature such as capillaries, grooves or channels in the struts, in which the coating composition can collect and be retained by surface tension.

The coating compositions described herein preferably remain on a stent, partially or in substantial part, after the stent has been introduced to the body, for at least several days and more preferably for several weeks. In one or more specific embodiments, the coating composition is a solid until it is placed in the body together with the stent, at which time it begins to melt to form a liquid, e.g., at 37° C. More preferably, the coating composition does not melt immediately upon insertion into the body, but melts upon reaching the site of its use.

As discussed above, one type of medical device suitable for use in connection with coatings of the present invention is an angioplasty balloon. The liquid coating compositions described herein preferably remain substantially intact on an angioplasty balloon during the insertion of the balloon through the body to the site of its use. Some of the coating composition will be transferred from the balloon to the hydrophobic plaque at the occluded site in the artery when the balloon is inflated at the site of an artery blockage. This is advantageous because the biologically active component in the coating composition will be directly transferred with the carrier onto the plaque. In this manner, the biologically active component can be delivered directly to its desired site of use. In a preferred embodiment, the coating compositions are hydrophobic. When hydrophobic coating compositions are used, they tend to dissolve faster than non-hydrophobic coating compositions after contacting the hydrophobic plaque and, thus, more readily release the biologically active component.

In another aspect, the invention can include a method of coating a stent. A specific embodiment of the method includes providing a stent, providing a coating composition comprising a biologically active component and a carrier component that has a melting point of about 50° C. or less, more preferably about 40° C. or less, most preferably body temperature (37° C.) or less, and applying the coating composition to the stent. In another embodiment, the invention includes a method that comprises providing a coating composition that includes a biologically active component and a liquid carrier component which has a viscosity of from about 0.1 to about 15000 cP, and applying the coating composition to the stent.

In a specific embodiment, the method of coating a stent comprises providing a stent, providing a coating composition comprising a blend of a substantially unreacted bioactive component and a polymeric or nonpolymeric carrier having a melting point of about 50° C. or less, and applying the coating composition to the stent. Providing to the coating composition may comprise mixing the bioactive component and a nonpolymeric liquid carrier. In one embodiment, the nonpolymeric liquid carrier comprises a C-6 to C-18 fatty acid, such as oleic acid or stearic acid. In another embodiment, the liquid carrier comprises a liquid selected from the group consisting of vitamin E, peanut oil, cottonseed oil, and mineral oil. In another embodiment, providing the coating composition may comprise mixing the bioactive component and a polymeric liquid carrier. In a further embodiment, providing the coating composition may include mixing an HMG-CoA reductase inhibitor, a low-melting polymer, and a solvent under conditions such that the HMG-CoA reductase inhibitor does not chemically react with the polymer, or does not react to any substantial extent, applying the mixture to the stent, and removing the solvent. Providing the coating composition may also include mixing the HMG-CoA reductase inhibitor, a polymer, and a solvent at a temperature of from about 20° C. to about 30° C., preferably at about 22° C. In another embodiment, providing a coating composition may include providing a solid coating comprising an HMG-CoA reductase inhibitor and a polymer.

In one or more specific embodiments, the invention can include a treatment method, comprising deploying a coated stent into a body lumen of a patient, the coated stent comprising a stent and a coating composition that comprises a carrier component and a bioactive component, the biodegradable component having a melting point of about 50° C. or less. In a preferred embodiment, the carrier is biodegradable, although biostable carriers may also be used. In other specific embodiments, the coated stent comprises a stent and a coating composition that includes a carrier component and a bioactive component, the carrier having a viscosity of from about 0.1 to about 15000. In yet another specific embodiment, the coated stent comprises a stent and a coating composition that includes a biodegradable carrier component and a bioactive component, and the carrier is in a solid state outside of a human body and a liquid inside of a human body.

In another aspect, the invention can include a treatment method comprising attaching a stent to a catheter, applying to the catheter and the stent a coating composition comprising a biodegradable carrier component having a melting point of about 50° C. or less and a bio active component, and deploying the coated stent into a body lumen of a patient.

In another aspect, the invention includes a method of treating an occluded artery comprising providing a stent, providing a coating composition comprising a low-melting nonpolymeric or polymeric carrier and a bioactive component in an amount effective to prevent or substantially reduce restenosis, applying the coating composition to the stent, and deploying the stent in the occluded artery at the site of occlusion. Providing a coating composition may comprise dissolving or suspending in a nonpolymeric liquid or low-melting carrier an amount of an HMG-CoA reductase inhibitor effective to prevent or substantially reduce restenosis. In another embodiment, providing a coating composition may comprise dissolving in a polymeric liquid or low-melting carrier an amount of an HMG-CoA reductase inhibitor effective to prevent or substantially reduce restenosis in an occluded vascular lumen. Where a polymeric carrier is provided, the HMG-CoA reductase inhibitor may be physically bound to the polymer, chemically bound to the polymer, or both. The coating composition may be a solution that comprises the HMG-CoA reductase inhibitor, the polymer, and a solvent. The solvent may be removed by, e.g., drying the stent or other methods known in the art. In another embodiment, the coating composition may comprise the HMG-CoA reductase inhibitor and a polymer having a melting point between 30° C. and 50° C., and applying the coating composition to the stent may comprise melting the coating composition, spraying the melted coating on the stent, and allowing the coating to solidify. The coating composition may include an amount of the HMG-CoA reductase inhibitor that is therapeutically effective for inhibiting regrowth of plaque or inhibiting restenosis. More particularly, the coating composition may comprise from about 1 wt % to about 50 wt % HMG-CoA reductase inhibitor, based on the total weight of the coating composition.

In another aspect, the invention can include a method of treating restenosis, comprising inserting a coated stent into a body lumen, the coated stent comprising a stent and a coating composition comprising a substantially unreacted HMG-CoA reductase inhibitor and a low-melting, nonpolymeric or polymeric carrier, which may be a liquid or a solid. In one embodiment, the coated stent releases the HMG-CoA reductase inhibitor in an amount sufficient to inhibit the proliferation of smooth muscle cells. In another embodiment, the coated stent releases the HMG-CoA reductase inhibitor in an amount sufficient to inhibit restenosis.

In another aspect, the invention may comprise a method of localized delivery of an HMG-CoA reductase inhibitor, comprising inserting a coated stent into a body lumen, the coated stent comprising a stent and a coating composition comprising a substantially unreacted HMG-CoA reductase inhibitor and a low-melting polymeric or nonpolymeric carrier. In one embodiment, the coated stent releases the HMG-CoA reductase inhibitor in an amount effective to inhibit the proliferation of smooth muscle cells. In another embodiment, the coated stent releases the HMG-CoA reductase inhibitor in an amount effective to inhibit restenosis.

In another aspect, the invention can include a coated stent, comprising a stent and a coating composition comprising a biologically active component and a biodegradable carrier component which may have a melting point of about 50° C. or less, and a catheter which can be coupled to the coated stent to form a treatment assembly.

In accordance with methods and compositions described herein, restenosis may be prevented or lessened using localized delivery of HMG-CoA reductase inhibitors from a liquid or low-melting carrier coupled to a stent placed in a body lumen. Preferably, metal stents are coated with a biocompatible coating composition comprising a carrier and an effective amount of an HMG-CoA reductase inhibitor. The coated stent can be deployed during any conventional percutaneous transluminal coronary angioplasty (PTCA) procedure. Controlled delivery from a stent of the active HMG-CoA reductase inhibitor, using a coating such as that described herein, in an effective amount, can inhibit the regrowth of plaque and prevent restenosis. While the stents shown and described in the various embodiments are vascular stents, any type of stent suitable for deployment in a body lumen of a patient may be used with the coatings described herein.

EXAMPLES

The following examples are included to demonstrate different illustrative embodiments or versions of the invention. However, those skilled in the art will, in light of the present disclosure, appreciate that many changes can be made in the specific embodiments which are disclosed and still obtain a like or similar result without departing from the spirit and scope of the invention.

Coronary stents were provided by Baylor Medical School and Sulzer Intratherapeutics. Poly(lactic acid)-co-poly(glycolic acid) (PLGA) polymer was purchased from Boehringer Ingelheim. Methylene chloride was purchased from Aldrich. Poly(ethylene-co-vinyl acetate) (EVA) copolymer was purchased from Aldrich or Polymer Sciences. Sulzer Carbomedics, Inc. provides medical grade silicone rubber.

Example 1

One hundred (100) mg PCL (poly caprolactone) polymer and 10 mg of cerivastatin were dissolved in 10 ml methylene chloride solution at room temperature. The solution was poured onto a glass plate and the solvent was allowed to evaporate for 12-24 hours. After almost complete removal of the solvent, the cerivastatin-loaded PCL film was removed from the glass plate and was cut to 1.5 cm by 1.5 cm size. The film was mounted on a Palmaz-Schatz coronary endovascular stent. Control PCL films were prepared in the following manner: 100 mg PCL (poly caprolactone) polymer was dissolved in 10 ml methylene chloride solution at room temperature. The solution was poured onto a glass plate and the solvent was allowed to evaporate for 12-24 hours. After almost complete removal of the solvent, the control PCL film was removed from the glass plate and was cut to 1.5 cm by 1.5 cm size. The control film was mounted on a Palmaz-Schatz coronary endovascular stent. Release profiles were obtained for the coated stents as shown in FIG. 6.

Example 2

100 mg EVA (ethylene-vinyl acetate) polymer and 10 mg of cerivastatin were dissolved in 10 ml methylene chloride solution at room temperature. The solution was poured onto a glass plate and the solvent was allowed to evaporate for 12-24 hours. After almost complete removal of the solvent, the cerivastatin-loaded EVA film was removed from the glass plate and was cut to 1.5 cm by 1.5 cm size. The film was mounted on a Palmaz-Schatz coronary endovascular stent. Control EVA films were prepared in the following manner: 100 mg EVA (ethylene-vinyl acetate) polymer was dissolved in 10 ml methylene chloride solution at room temperature. The solution was poured onto a glass plate and the solvent was allowed to evaporate for 12-24 hours. After almost complete removal of the solvent, the control EVA film was removed from the glass plate and was cut to 1.5 cm by 1.5 cm size. The control film was mounted on a Palmaz-Schatz coronary endovascular stent. Release profiles were obtained for the coated stents as shown in FIG. 5.

Example 3

A 0.6% solution of polycaprolactone dissolved in methylene chloride was prepared at room temperature. The solution was sprayed onto a Sulzer Intratherapeutics nitinol Protege model endovascular stent (6 mm×20 mm) using a semi-automated nebulizer apparatus. The nebulizer spray system provided a means of rotating and traversing the length of the stent at a controlled rate. The traversing component of the apparatus contained a glass nebulizer system that applied nebulized polycaprolactone solution to the stent at a rate of 3 ml per minute. Once applied, the 10 mg polymer coating was "reflowed" by application of 60° C. heated air for approximately 5 seconds. The process of reflowing the polymer provides better adherence to the stent surface. A drug-loaded polymer coating can be provided using this technique by first preparing a 1%-20% cerivastatin/polymer solution in methylene chloride with subsequent application to the stent surface using the same nebulizer coating system.

Example 4

A 1% solution of uncured two-part silicone rubber dissolved in trichloroethylene was applied to a "Protege" nitinol stent in the manner described in Example 3. The coated stent was dried at room temperature for 15 minutes to allow the trichloroethylene to evaporate. Once 10 mg of silicone was coated onto the stent, the composite device containing both uncured polymer and nitinol was heated in a vacuum oven for a period of four hours in order to crosslink the silicone coating. After the coated stents were removed from the oven and allowed to cool for a period of 1 hour, cerivastatin was loaded into the silicone coating by the following method. Three mg of cerivastatin was dissolved in 300 µl of methylene chloride at room temperature. A volume of 100 µl of methylene chloride was applied to the silicone coating of each stent in dropwise fashion. In this manner, each stent was loaded with 1 mg cerivastatin, for a final concentration of 10% w/w. The crosslinked silicone absorbed the drug/solvent solution, where the solvent subsequently evaporated at room temperature, leaving behind the drug entrapped within the silicone. By this method, a diffusion-based release system for cerivastatin was created. A release profile was obtained for the coated stent as shown in FIG. 7.

Example 5

A 10% w/w solution of cerivastatin in vitamin E was created by the following method. Four mg of cerivastatin was dissolved in 100 µl of methylene chloride. This solution was added to 36 mg of liquid vitamin E and mixed manually by stirrer. The solution was allowed to stand at room temperature for 1 hour to enable the methylene chloride to evaporate from the solution. The resulting cerivastatin/vitamin E mixture was used to coat three Protg model stents by simple surface application. Approximately 10-12 mg of vitamin E and drug was deposited on each stent. A release profile was obtained for the coated stent as shown in FIG. 8.

Example 6

A 50 ml round bottom flask with a Teflon coated magnetic stirrer is flame dried under repeated cycles of vacuum and dry nitrogen. Two (2) g trimethylol propane, 11.68 g D,L-lactide, and 0.20 mg stannous octoate are charged to the flask. The flask is then heated to 165° C. for 16 hours and then cooled. The liquid product is dissolved in 30 ml toluene and precipitated in large excess cold hexane. The precipitated polymer, which is a liquid at room temperature, is isolated and can be used in coating stents.

Example 7

Polycaprolactone diol (MW 2000) (PCL 2000) is purchased from Aldrich. This polymer melts at approximately 60-70° C., depending upon its thermal (cooling) history and the degree of crystallinity in the bulk polymer. This polymer is insoluble in water.

Example 8

Polycaprolactone triol (MW 300) (PCL 300) is purchased from Aldrich and used as received. This polymer is liquid at room temperature and is immiscible with water.

Example 9

One (1) g of PCL 300, a liquid at room temperature, and 50 mg of PCL 2000, a solid at room temperature, are mixed to obtain a viscous mixture which is liquid at room temperature. The viscosity of the mixture is greater than the viscosity of PCL 300.

Example 10

One (1) g PCL 300 (See Example 6) and 10 mg rifampin are added to a 2 ml glass vial. A 7×20 mm metal stent (Lot R0036203, Sulzer Intra Therapeutics) is added to the vial. The excess liquid on the surface of the stent is removed. The coated stent is then sterilized using ethylene oxide, compressed, and mounted on a balloon angioplasty catheter. It is then deployed at a diseased site in an artery using standard balloon angioplasty techniques and implanted at the site of reduced blood flow or obstruction of the artery. The hydrophobic liquid layer on the stent releases the drug in a controlled fashion.

Example 11

One (1) g PCL 300 (see Example 6) and 10 mg rifampin are added to a 2 ml glass vial. A paint brush is used to coat an angioplasty balloon surface with the PCL 300-rifampin mixture. The balloon is sterilized using ethylene oxide, compressed, and mounted on the balloon angioplasty catheter. It is then deployed at a diseased site in a coronary artery using standard balloon angioplasty technique. The coated balloon is expanded at the site of reduced blood flow or obstruction in the artery. The contact of the balloon surface with the arterial lumen wall transfers a portion of the liquid coating onto the wall surface as well as onto the material obstructing the arterial lumen. The hydrophobic liquid layer is transferred onto the lumen walls and onto the obstructing material, delivering the bioactive compound in a controlled manner.

In preferred embodiments, the controlled release studies were done to determine the integrity and activity of cerivastatin released from stents coated with polymer and cerivastatin. Stents coated according to the process of Example 2 were immersed in an Eppendorf tube containing 1 ml phosphate buffered saline (PBS) and incubated on a rotator in a 37° C. oven. Buffer exchanges were performed at 1, 2, and 4 days following immersion in PBS. Collected samples were assayed for the spectral characteristics of cerivastatin using a UV-VIS spectrophotometer. Cerivastatin released from an EVA and cerivastatin coated stent such as the stent of Example 2 and pure cerivastatin in deionized water had almost identical UV-VIS spectra, as shown in FIG. 4, suggesting that the cerivastatin released from the stent was unaltered and thus remained biologically active.

The release of cerivastatin from stents coated according to the process of Example 2 was monitored over 7 days, as shown in FIG. 5. An EVA and cerivastatin coated stent such as the stent of Example 2 released >20 μg/ml cerivastatin per day, which is significantly higher than the 0.5 .mu.g/ml concentration needed to inhibit proliferation of smooth muscle cells. Thus, stents produced according to this invention release a sufficient amount of cerivastatin to inhibit the proliferation of smooth muscle cells which occurs during restenosis.

The release of cerivastatin from stents coated with polycaprolactone film according to the process of Example 1 was monitored over 80 days, as shown in FIG. 6. A polycaprolactone and cerivastatin coated stent such as the stent of Example 1 released >20 μg/ml cerivastatin per day. The release of cerivastatin from stents according to the process of Example 4 was monitored over 20 days, as shown in FIG. 7. A cerivastatin and silicone coated stent such as the stent of Example 4 released >20 μg/ml cerivastatin per day.

The release of cerivastatin from stents according to the process of Example 5 was monitored over 11 days, as shown in FIG. 8. A liquid vitamin E and cerivastatin coated stent such as the stents of Example 5 released >20 μg/ml cerivastatin per day.

While the foregoing is directed to embodiments of the present invention, other and further embodiments of the invention may be devised without departing from the basic scope thereof, and the scope thereof is determined by the claims that follow, including equivalents.

What is claimed is:

1. A coated stent comprising:
   a stent; and
   a coating on the stent, the coating comprising:
   an HMG-CoA reductase inhibitor in an amount between about 1 wt. % and about 50 wt. %, based on a total weight of the coating; and
   a carrier for the HMG-CoA reductase inhibitor,
   wherein coating is configured to release the HMG-CoA reductase from the stent at a rate of >20 μg/ml per day.

2. The coated stent of claim 1, wherein the coating comprises the HMG-CoA reductase inhibitor in an amount between about 5 wt. % and about 30 wt. %, based on a total weight of the coating.

3. The coated stent of claim 1, wherein the coating comprises the HMG-CoA reductase inhibitor in an amount between about 2 wt. % and about 20 wt. %, based on a total weight of the coating.

4. The coated stent of claim 1, wherein the HMG-CoA reductase inhibitor is selected from a group consisting of: cerivastatin, atorvastatin, simvastatin, fluvastatin, lovastatin, and pravastatin.

5. The coated stent of claim 1, wherein the HMG-CoA reductase inhibitor is cerivastatin.

6. The coated stent of claim 1, wherein the coating further comprises a restenosis inhibitor which is not an HMG-CoA reductase inhibitor.

7. The coated stent of claim 1, wherein the carrier is non-reactive with the HMG-CoA reductase inhibitor.

8. The coated stent of claim 1, wherein the carrier comprises a polymeric carrier that is physically bound to the HMG-CoA reductase inhibitor.

9. The coated stent of claim 1, wherein the carrier comprises a polymeric carrier that is chemically bound to the HMG-CoA reductase inhibitor.

10. The coated stent of claim 1, wherein the carrier comprises a polymeric biodegradable carrier.

11. The coated stent of claim 1, wherein the carrier comprises a nonpolymeric carrier.

12. The coated stent of claim 11, wherein the nonpolymeric carrier is selected from a group consisting of: Vitamin E, Vitamin E acetate, Vitamin E succinate, oleic acid, peanut oil and cottonseed oil.

13. The coated stent of claim 1, wherein the carrier is liquid at body temperature.

14. The coated stent of claim 1, wherein the carrier is solid at body temperature.

15. The coated stent of claim 1, wherein the coating further comprises one or more bioactive compounds selected from a group consisting of: paclitaxel, paclitaxel analogs, actinomycin D, actinomycin D analogs, rapamycin, rapamycin analogs, and mixtures thereof.

16. A coated stent comprising:
    a stent; and
    a coating comprising:
    an HMG-CoA reductase inhibitor in an amount between about 1 wt. % and about 50 wt. %, based on a total weight of the coating; and
    a polymeric biodegradable carrier for the HMG-CoA reductase inhibitor, the polymeric biodegradable carrier comprising a polymer selected from polycaprolactone, ethylene-vinyl acetate polymer, and a two-part silicone rubber,
    wherein the coating is configured to release the HMG-CoA reductase Inhibitor from the stent at a rate of >20 μg/ml per day.

17. The coated stent of claim 16, wherein the coating comprises the HMG-CoA reductase inhibitor in an amount between about 5 wt. % and about 30 wt. %, based on a total weight of the coating composition.

18. The coated stent of claim 16, wherein the coating comprises the HMG-CoA reductase inhibitor in an amount between about 2 wt. % and about 20 wt. %, based on a total weight of the coating composition.

19. The coated stent of claim 16, wherein the HMG-CoA reductase inhibitor is selected from a group consisting of: cerivastatin, atorvastatin, simvastatin, fluvastatin, lovastatin, and pravastatin.

20. The coated stent of claim 16, wherein the coating further comprises a restenosis inhibitor which is not an HMG-CoA reductase inhibitor.

21. The coated stent of claim 16, wherein the coating further comprises one or more bioactive compounds selected from a group consisting of: paclitaxel, paclitaxel analogs, actinomycin D, actinomycin D analogs, rapamycin, rapamycin analogs, and mixtures thereof.

* * * * *